United States Patent
Zhu et al.

(10) Patent No.: US 10,378,035 B2
(45) Date of Patent: Aug. 13, 2019

(54) SYNTHESIS OF TRANSCRIPTS USING SYN5 RNA POLYMERASE

(71) Applicant: President and Fellows of Harvard College, Cambridge, MA (US)

(72) Inventors: Bin Zhu, Malden, MA (US); Charles C. Richardson, Newton, MA (US); Stanley Tabor, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 330 days.

(21) Appl. No.: 15/132,645

(22) Filed: Apr. 19, 2016

(65) Prior Publication Data

US 2016/0312260 A1  Oct. 27, 2016

Related U.S. Application Data

(60) Provisional application No. 62/150,885, filed on Apr. 22, 2015.

(51) Int. Cl.
| | |
|---|---|
| C12P 19/34 | (2006.01) |
| C12P 21/00 | (2006.01) |
| C12N 15/11 | (2006.01) |
| C12N 15/113 | (2010.01) |
| C12N 15/115 | (2010.01) |

(52) U.S. Cl.
CPC ............. *C12P 19/34* (2013.01); *C12N 15/113* (2013.01); *C12N 15/115* (2013.01); *C12Y 207/07006* (2013.01); *C12N 2310/12* (2013.01); *C12N 2310/14* (2013.01); *C12N 2310/16* (2013.01); *C12N 2310/322* (2013.01); *C12N 2330/50* (2013.01)

(58) Field of Classification Search
None
See application file for complete search history.

(56) References Cited

U.S. PATENT DOCUMENTS

2016/0369248 A1* 12/2016 Richardson .......... C12Q 1/6895

OTHER PUBLICATIONS

Pope et al. Genome Sequence, Structural Proteins, and Capsid Organization of the Cyanophage Syn5: A "Horned" Bacteriophage of Marine Synechococcus. May 11, 2007. J. Mol. Biol. vol. 368, No. 4, p. 966-981. (Year: 2007).*

* cited by examiner

*Primary Examiner* — Channing S Mahatan
(74) *Attorney, Agent, or Firm* — Banner & Witcoff, Ltd.

(57) ABSTRACT

Methods of in vitro transcription using cyanophage Syn5 RNA polymerase (RNAP) or mutants thereof and transcription conditions are provided.

61 Claims, 9 Drawing Sheets

Specification includes a Sequence Listing.

FIG. 2A (SEQ ID NO:72)

FIG. 2B (SEQ ID NO:55)

T17 pppGGAGAAGAAUUU...
T18 pppGGAGAAGAACCC...
(SEQ ID NO:69-70)

T28
T4  pppGGAGAAGAAGAA...
(SEQ ID NO:71)

(SEQ ID NO:73) Original seq. CCA TTG GGC ACC CGT AAG
(SEQ ID NO:74) Modified seq. CCT CTT GGT ACG CGC AAG
                              Pro Leu Gly Thr Arg Lys

FIG. 9A
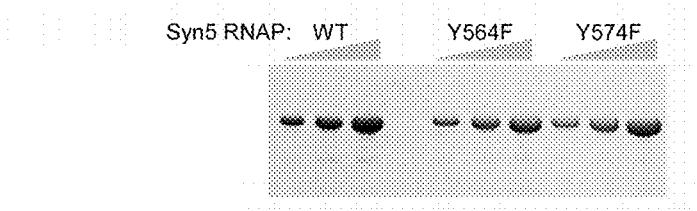
FIG. 9B
FIG. 10
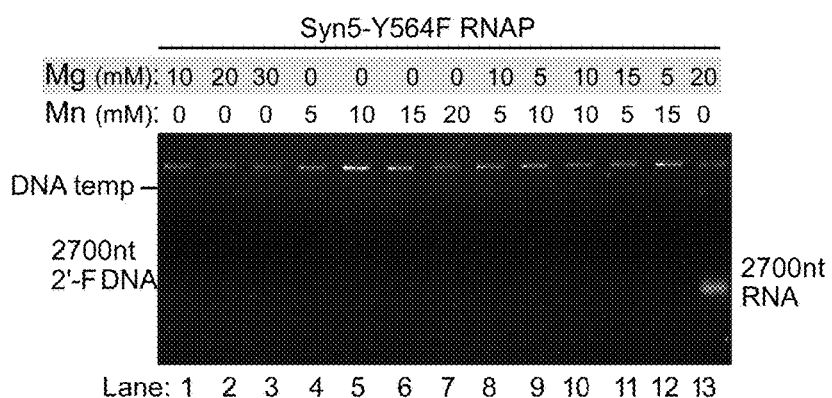

SYNTHESIS OF TRANSCRIPTS USING SYN5 RNA POLYMERASE

RELATED APPLICATION DATA

This application claims the benefit of U.S. provisional application Serial No. 62/150,885 filed Apr. 22, 2015, hereby incorporated by reference herein in its entirety.

FIELD

The present invention relates in general to SynS RNAP and mutants thereof to make transcripts.

BACKGROUND

2'-F RNAs are used widely in studies of ribozymes, the selection of aptamers, and in RNA interference. See, Pallan, P. S., Greene, E. M., Jicman, P. A., Pandey, R. K., Manoharan, M., Rozners, E. and Egli, M. (2011) Unexpected origins of the enhanced pairing affinity of 2'-fluoro-modified RNA. Nucleic Acids Res., 39, 3482-3495; Morrissey, D. V., Lockridge, J. A., Shaw, L., Blanchard, K., Jensen, K., Breen, W., Hartsough, K., Machemer, L., Radka, S., Jadhav, V., et al. (2005) Potent and persistent in vivo anti-HBV activity of chemically modified siRNAs. Nat. Biotechnol., 23, 1002-1007; Layzer, J. M., McCaffrey, A. P., Tanner, A. K., Huang, Z., Kay, M. A. and Sullenger, B. A. (2004) In vivo activity of nuclease-resistant siRNAs. RNA, 10, 766-771; Khati, M., Schüman, M., Ibrahim, J., Sattentau, Q., Gordon, S. and James, W. (2003) Neutralization of infectivity of diverse R5 clinical isolates of human immunodeficiency virus type 1 by gp120-binding 2'F-RNA aptamers. J. Virol., 77, 12692-12698; Chiu, Y. L. and Rana, T. M. (2003) siRNA function in RNAi: a chemical modification analysis. RNA, 9, 1034-1048; Sabahi, A., Guidry, J., Inamati, G. B., Manoharan, M. and Wittung-Stafshede, P. (2001) Hybridization of 2'-ribose modified mixed-sequence oligonucleotides: thermodynamic and kinetic studies. Nucleic Acids Res., 29, 2163-2170; Ruckman, J., Green, L. S., Beeson, J., Waugh, S., Gillette, W. L., Henninger, D. D., Claesson-Welsh L. and Janjić, N. (1998) 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. J. Biol. Chem., 273, 20556-20567; and Pieken, W. A., Olsen, D. B., Benseler, F., Aurup, H. and Eckstein, F. (1991) Kinetic characterization of ribonuclease-resistant 2'-modified hammerhead ribozymes. Science, 253, 314-317.

2'-F RNAs have improved properties such as resistance to cleavage by RNase A. See Cuchillo, C. M., Nogués, M. V. and Raines, R. T. (2011) Bovine pancreatic ribonuclease: Fifty years of the first enzymatic reaction mechanism. Biochemistry, 50, 7835-7841.

2'-F RNA can be synthesized enzymatically. See, Ono, T., Scalf, M. and Smith, L. M. (1997) 2'-Fluoro modified nucleic acids: polymerase-directed synthesis, properties and stability to analysis by matrix-assisted laser desorption/ionization mass spectrometry. Nucleic Acids Res., 25, 4581-4588; Friedman, A. D., Kim, D., Liu, R. (2015) Highly stable aptamers selected from a 20-fully modified fGmH RNA library for targeting biomaterials. Biomaterials, 36, 110-123; and Cozens, C., Pinheiro, V. B., Vaisman, A., Woodgate, R. and Holliger, P. (2012) A short adaptive path from DNA to RNA polymerases. Proc. Natl. Acad. Sci. U.S.A., 109, 8067-8072. A standard commercially available enzyme for the preparation of 2'-F RNA is the bacteriophage T7 RNA polymerase Y639F in which tyrosine 639 is replaced with phenylalanine. See Sousa R. and Padilla R. (1995) A mutant T7 RNA polymerase as a DNA polymerase. EMBO J., 14, 4609-4621. The Y639F alteration in T7 RNA polymerase reduces discrimination between non-canonical and canonical nucleoside triphosphates. However such discrimination is still substantial, especially when multiple 2'-modified NTPs or 2'-modified GTP (the strict initiation nucleotide for T7 RNA polymerase) are included in the reaction. See Sousa R. and Padilla R. (1995) A mutant T7 RNA polymerase as a DNA polymerase. EMBO J., 14, 4609-4621; and Padilla R. and Sousa R. (1999) Efficient synthesis of nucleic acids heavily modified with non-canonical ribose 2'-groups using a mutant T7 RNA polymerase (RNAP). Nucleic Acids Res., 27, 1561-1563.

SUMMARY

Aspects of the present disclosure are directed to the use of a single-subunit RNA polymerase from marine cyanophage Syn5 (Syn5 RNAP) for in vitro transcription. See Zhu, B., Tabor, S., Raytcheva, D. A., Hernandez, A., King, J. A. and Richardson, C. C. (2013) The RNA polymerase of marine cyanophage Syn5. J. Biol. Chem., 288, 3545-3552 hereby incorporated by reference in its entirety.

A single subunit DNA-dependent RNAP was identified and purified to apparent homogeneity from cyanophage Syn5 that infects the marine cyanobacteria Synechococcus. Syn5 is homologous to bacteriophage T7 that infects E. coli. Using the purified enzyme its promoter has been identified by examining transcription of segments of Syn5 DNA and sequencing the 5'-termini of the transcripts. Only two Syn5 RNAP promoters, having the sequence 5'-ATTGGGCAC-CCGTAA-3' (SEQ ID NO:1), are found within the Syn5 genome. One promoter is located within the Syn5 RNAP gene and the other is located close to the right genetic end of the genome.

Aspects of the present disclosure are directed to the use of altered Syn5 RNAP Y564F mutant which has the sequence of the wild type Syn5 RNAP and where tyrosine 564 is replaced with phenylalanine. Altered Syn5 RNAP may also be referred to as mutant Syn5 RNAP or Syn5 RNAP Y564F.

Syn5 RNAP catalyzes RNA synthesis over a wide range of temperature and salinity. Its processivity is greater than 30,000 nucleotides ("nt") without the appearance of intermediate products. Most significantly, Syn5 RNAP produces precise run-off transcripts with homogeneity in their 3' termini. This latter property makes it advantageous for production of RNAs that require precise 3'-termini such as tRNAs and RNA fragments for subsequent assembly.

Syn5 RNAP has a relatively short promoter sequence, a high tolerance to salt, and high processivity. RNA synthesis catalyzed by Syn5 RNAP results in precise run-off with the products lacking non-based additional nucleotides, i.e. lacking an N+1 product, which impedes the function of these RNAs in applications where the precise 3'-terminus of the RNA is critical. These applications include the synthesis of tRNA molecules, RNA probes, RNA primers, genomes of some RNA viruses, RNAs for ligation and assembly, and specific RNAs for structure studies. Accordingly, embodiments of the present disclosure include the use of Syn5 RNAP and mutants thereof in methods of making RNA, such as RNA transcripts having a precise 3'-terminus, under the conditions disclosed herein. In yet other aspects, greater than about 90% of the transcripts contain homogeneous 3' ends, greater than about 95% of the transcripts contain homogeneous 3' ends, or greater than about 99% of the transcripts contain homogeneous 3' ends. In other aspects, greater than about 90% of the transcripts contain precisely terminated 3' ends, greater than about 95% of the transcripts contain precisely terminated 3' ends, or greater than about 99% of the transcripts contain precisely terminated 3' ends. In still other aspects, greater than about 90% of the transcripts lack a nucleotide overhang at the 3' ends, greater than about 95% of the transcripts lack a nucleotide overhang at the 3' ends, or greater than about 99% of the transcripts lack a nucleotide overhang at the 3' ends. In other aspects, less than 20% of the transcripts contain a nucleotide overhang at their 3' ends, less than 10% of the transcripts contain a nucleotide overhang at their 3' ends, less than 5% of the transcripts contain a nucleotide overhang at their 3' ends or less than 1% of the transcripts contain a nucleotide overhang at their 3' ends. The method of claim 1, wherein less than 20% of the transcripts contain a nucleotide overhang at their 3' ends. In yet other aspects, less than 10% of the transcripts contain a nucleotide overhang at their 3' ends, less than 5% of the transcripts contain a nucleotide overhang at their 3' ends, or less than 1% of the transcripts contain a nucleotide overhang at their 3' ends.

According to one aspect, a method is provided for performing in vitro transcription comprising the steps of combining a double stranded nucleic acid including a template strand and a coding strand, a cyanophage Syn5 RNAP or mutant thereof, one or more nucleotides, and optionally one or more modified nucleotides and optionally one or more of 2'-fluoro-dCTP, or 2'-fluoro-dUTP under conditions suitable for producing a transcript, and producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, wherein nt is dCMP, dGMP, dAMP or dTMP and wherein nucleotides $nt_1$-$nt_2$-$nt_3$-$nt_4$-$nt_5$-$nt_6$-$nt_7$-$nt_8$-$nt_9$ include no more than 2 dTMPs or no more than 2 dCMPs with the remaining nucleotides being one or more of dGMP or dAMP with the proviso that nucleotides $nt_1$-$nt_2$-$nt_3$-$nt_4$-$nt_5$-$nt_6$-$nt_7$-$nt_8$-$nt_9$ cannot include 2 dTMPs and 2 dCMPs.

According to one aspect, the mutant is Syn5 Y564F. According to one aspect, the conditions suitable for producing a transcript include the presence of $Mn^{2+}$ in a concentration range of 5 mM to 20 mM or $Mg^{2+}$ in a concentration range of 10 mM to 20 mM. According to one aspect, wherein the conditions suitable for producing a transcript include the presence of $Mg^{2+}$ in a concentration range of 10 mM to 20 mM and $Mn^{2+}$ in a concentration range of 5 mM to 20 mM. According to one aspect, the conditions suitable for producing a transcript include the presence of $Mg^{2+}$ in a concentration of 10 mM and $Mn^{2+}$ in a concentration of 5 mM. According to one aspect, the transcript includes one or more of 2'-fluoro-dCMP or 2'-fluoro-dUMP. According to one aspect, nucleotides $nt_1$-$nt_2$-$nt_3$-$nt_4$-$nt_5$-$nt_6$-$nt_7$-$nt_8$-$nt_9$ include no more than 1 dCMP or no more than 1 dTMP with the remaining nucleotides being one or more of dGMP or dAMP. According to one aspect, nucleotides $nt_1$-$nt_2$-$nt_3$-$nt_4$-$nt_5$-$nt_6$-$nt_7$-$nt_8$-$nt_9$ include no dCMP and no more than 2 dTMPs with the remaining nucleotides being one or more of dGMP or dAMP. According to one aspect, nucleotides $nt_1$-$nt_2$-$nt_3$-$nt_4$-$nt_5$-$nt_6$-$nt_7$-$nt_8$-$nt_9$ include no dTMP and no more than 2 dCMPs with the remaining nucleotides being one or more of dGMP or dAMP. According to one aspect, nucleotides $nt_1$-$nt_2$-$nt_3$-$nt_4$-$nt_5$-$nt_6$-$nt_7$-$nt_8$-$nt_9$ include no dTMP and no more than 3 dCMPs. According to one aspect, nucleotides $nt_1$-$nt_2$-$nt_3$-$nt_4$-$nt_5$-$nt_6$-$nt_7$-$nt_8$-$nt_9$ include no dCMP and no dTMP and with the remaining nucleotides being one or more of dGMP or dAMP. According to one aspect, nucleotides $nt_1$-$nt_2$-$nt_3$ include no dTMP. According to one aspect, nucleotides $nt_1$-$nt_2$-$nt_3$ are dGMP-dGMP-dAMP, dGMP-dAMP-dAMP, dAMP-dGMP-dAMP, dGMP-dCMP-dAMP, or dCMP-dAMP-dGMP. According to one aspect, nucleotides $nt_1$-$nt_2$-$nt_3$-$nt_4$-$nt_5$-$nt_6$-$nt_7$-$nt_8$-$nt_9$ include no dAMP in series of 4 or more. According to one aspect, nucleotides $nt_1$-$nt_2$-$nt_3$-$nt_4$-$nt_5$-$nt_6$-$nt_7$-$nt_8$-$nt_9$ or portions thereof beginning at $nt_1$ are dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dGMP, dGMP-dCMP-dAMP-dGMP-dAMP-dGMP-dAMP, dGMP-dCMP-dAMP-dGMP-dAMP-dAMP-dAMP-dGMP, dGMP-dCMP-dAMP-dGMP-dAMP-dAMP-dAMP-dGMP-dAMP or dGMP-dCMP-dAMP-dGMP-dAMP-dAMP-dGMP-dAMP-dAMP. According to one aspect, the transcript is mRNA, tRNA, rRNA, miRNA, siRNA, snRNA, snoRNA, a ribozyme, an aptamer or an RNA fragment. According to one aspect, conditions suitable for producing a transcript include the presence of salt at a concentration of at least about 100 mM. According to one aspect, conditions suitable for producing a transcript include the presence of a salt at a concentration of at least about 160 mM. According to one aspect, conditions suitable for producing a transcript include the presence of a salt at a concentration of at least about 200 mM. According to one aspect, conditions suitable for producing a transcript include the presence of a salt at a concentration of about 250 mM. According to one aspect, the conditions suitable for producing a transcript include the presence of KCl or NaCl. According to one aspect, conditions suitable for producing a transcript include a temperature within the range of 4° C. and 37° C. According to one aspect, conditions suitable for producing a transcript include a temperature within the range of 10° C. and 25° C. According to one aspect, conditions suitable for producing a transcript include a temperature within the range of 14° C. and 22° C. According to one aspect, conditions suitable for producing a transcript include a temperature of 16° C. According to one aspect, the one or more modified nucleotides is 2'-F-dATP, 2'-F-dGTP, 2'-$NH_2$-dATP, 2'-$NH_2$-dGTP, 2'-$NH_2$-dCTP, 2'-$NH_2$-dUTP, 2'-OMe-dATP, 2'-OMe-dGTP, 2'-OMe-dCTP, or 2'-OMe-dUTP. According to one aspect, the cyanophage Syn5 RNAP or mutant thereof includes a heterologous polypeptide sequence. According to one aspect, the cyanophage Syn5 RNAP or mutant thereof includes a protein tag selected from the group consisting of one or any combination of Avi tag, calmodulin tag, FLAG tag, HA tag, His tag, Myc tag, S tag, SBP tag, Softag 1, Softag 3, V5 tag, Xpress tag, Isopeptag, SpyTag, biotin carboxyl carrier protein tag, glutathione-s-tranferase tag, green fluorescent protein tag, maltose binding protein tag, Nus tag, streptavidin tag, streptactin tag, and thioredoxin tag. According to one aspect, the cyanophage Syn5 RNAP or mutant thereof includes a removable protein tag. According to one aspect, the transcripts are greater than about 10,000 nucleotides in length. According to one aspect, the transcripts are greater than about 20,000 nucleotides in length. According to one aspect, the transcripts are greater than about 30,000 nucleotides in length. According to one aspect, greater than about 90% of the transcripts contain homogeneous 3' ends. According to one aspect, greater than about 95% of the transcripts contain homogeneous 3' ends. According to one aspect, greater than about 99% of the transcripts contain homogeneous 3' ends. According to one aspect, greater than about 90% of the transcripts contain precisely terminated 3' ends. According to one aspect, greater than about 95% of the transcripts contain precisely terminated 3' ends. According to one aspect, greater than about 99% of the transcripts contain precisely terminated 3' ends. According to one aspect, greater than about 90% of the transcripts lack a nucleotide overhang at the 3' ends. According to one aspect, greater than about 95% of the transcripts lack a nucleotide overhang at the 3' ends. According to one aspect, greater than about 99% of the transcripts lack a nucleotide overhang at the 3' ends. According to one aspect, the cyanophage Syn5 RNA polymerase is an isolated cyanophage Syn5 RNA polymerase. According to one aspect, the cyanophage Syn5 RNA polymerase is a purified cyanophage Syn5 RNA polymerase. According to one aspect, the cyanophage Syn5 RNA polymerase is a synthetic cyanophage Syn5 RNA polymerase. According to one aspect, less than 20% of the transcripts contain a nucleotide overhang at their 3' ends. According to one aspect, less than 10% of the transcripts contain a nucleotide overhang at their 3' ends. According to one aspect, less than 5% of the transcripts contain a nucleotide overhang at their 3' ends. According to one aspect, less than 1% of the transcripts contain a nucleotide overhang at their 3' ends. According to one aspect, the nucleic acid template sequence is a DNA template sequence and the transcript includes fewer than three 2'-modified nucleotides within the first 12 nucleotides of the transcript and wherein the fewer than three 2'-modified nucleotides within the first 12 nucleotides are non-consecutive. According to one aspect, the nucleic acid template sequence includes a sequence which when transcribed by the cyanophage Syn5 RNAP produces a transcript including fewer than three 2'-modified nucleotides within the first 12 nucleotides of the transcript.

According to one aspect, a method of performing in vitro transcription is provided including combining a double stranded nucleic acid including a template strand and a coding strand, a cyanophage Syn5 RNAP or mutant thereof, one or more nucleotides, and optionally one or more modified nucleotides and optionally one or more of 2'-fluoro-dCTP, or 2'-fluoro-dUTP under conditions suitable for producing a transcript, and producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, and wherein the conditions suitable for producing a transcript include the presence of $Mn^{2+}$ in a concentration range of 5 mM to 20 mM. According to one aspect, the mutant is Syn5 Y564F. According to one aspect, the conditions suitable for producing a transcript include the presence of $Mg^{2+}$ in a concentration range of 10 mM to 20 mM. According to one aspect, the conditions suitable for producing a transcript include the presence of $Mg^{2+}$ in a concentration of 10 mM and $Mn^{2+}$ in a concentration of 5 mM. According to one aspect, the transcript includes one or more of 2'-fluoro-dCMP or 2'-fluoro-dUMP. According to one aspect, the one or more modified nucleotides is 2'-F-dATP, 2'-F-dGTP, 2'-$NH_2$-dATP, 2'-$NH_2$-dGTP, 2'-$NH_2$-dCTP, 2'-$NH_2$-dUTP, 2'-OMe-dATP, 2'-OMe-dGTP, 2'-OMe-dCTP, or 2'-OMe-dUTP. According to one aspect, the transcript includes one or more of 2'-F-dAMP, 2'-F-dGMP, 2'-$NH_2$-dAMP, 2'-$NH_2$-dGMP, 2'-$NH_2$-dCMP, 2'-$NH_2$-dUMP, 2'-OMe-dAMP, 2'-OMe-dGMP, 2'-OMe-dCMP, or 2'-OMe-dUMP.

According to one aspect, a method of performing in vitro transcription is provided including combining a double stranded nucleic acid including a template strand and a coding strand, a cyanophage Syn5 RNAP Y564F mutant, one or more nucleotides, and optionally one or more modified nucleotides and optionally one or more of 2'-fluoro-dCTP, or 2'-fluoro-dUTP under conditions suitable for producing a transcript, and producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, and wherein the conditions suitable for producing a transcript include the presence of $Mn^{2+}$ in a concentration range of 15 mM to 20 mM. According to one aspect, the conditions suitable for producing a transcript include the presence of $Mg^{2+}$ in a concentration range of 15 mM to 20 mM and the presence of $Mn^{2+}$ in a concentration range of 15 mM to 20 mM. According to one aspect, the transcript includes one or more of 2'-fluoro-dCMP or 2'-fluoro-dUMP. According to one aspect, the one or more modified nucleotides is 2'-F-dATP, 2'-F-dGTP, 2'-$NH_2$-dATP, 2'-$NH_2$-dGTP, 2'-$NH_2$-dCTP, 2'-$NH_2$-dUTP, 2'-OMe-dATP, 2'-OMe-dGTP, 2'-OMe-dCTP, or 2'-OMe-dUTP. According to one aspect, the transcript includes one or more of 2'-F-dAMP, 2'-F-dGMP, 2'-$NH_2$-dAMP, 2'-$NH_2$-dGMP, 2'-$NH_2$-dCMP, 2'-$NH_2$-dUMP, 2'-OMe-dAMP, 2'-OMe-dGMP, 2'-OMe-dCMP, or 2'-OMe-dUMP.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more nucleotides, and optionally one or more modified nucleotides and optionally one or more of 2'-fluoro-dCTP, or 2'-fluoro-dUTP under conditions suitable for producing a transcript, and producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, wherein the first 9 nucleotides are altered to include beginning at $nt_1$ one of dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dAMP-dGMP, dGMP-dCMP-dAMP-dGMP-dAMP-dAMP-dGMP-dAMP or dGMP-dCMP-dAMP-dGMP-dAMP-dAMP-dGMP-dAMP-dAMP.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more nucleotides, and optionally one or more modified nucleotides and optionally one or more of 2'-fluoro-dCTP, or 2'-fluoro-dUTP under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, wherein one or more of dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dAMP-dGMP, dGMP-dCMP-dAMP-dGMP-dAMP-dAMP-dGMP-dAMP or dGMP-dCMP-dAMP-dGMP-dAMP-dAMP-dGMP-dAMP-dAMP is added to the coding strand after the promoter sequence and before the initiation sequence to create an altered initiation sequence of 12 nucleotides after the promoter sequence with complementary nucleotides added to the template strand, and producing a transcript.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more nucleotides, and optionally one or more modified nucleotides and optionally one or more of 2'-fluoro-dCTP, or 2'-fluoro-dUTP under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, wherein one or more of sequence dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dGMP, dGMP-dCMP-dAMP-dGMP-dAMP-dAMP-dAMP-dGMP-dAMP or dGMP-dCMP-dAMP-dGMP-dAMP-dAMP-dGMP-dAMP-dAMP coupled to a removable RNA element is added to the coding strand after the promoter sequence and before the initiation sequence to create an altered initiation sequence of 12 nucleotides after the promoter sequence with complementary nucleotides added to the template strand, and producing a transcript. According to one aspect, the removable RNA element is a ribozyme. According to one aspect, the ribozyme and the added sequence are removed from the transcript.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same rXMP where X is A, G, C, T or U within the first 9 nt, wherein one or more of sequence dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dGMP, dGMP-dCMP-dAMP-dGMP-dAMP-dAMP-dAMP-dGMP-dAMP or dGMP-dCMP-dAMP-dGMP-dAMP-dAMP-dGMP-dAMP-dAMP is added to the coding strand after the promoter sequence and before the initiation sequence to create an altered initiation sequence of 12 nucleotides after the promoter sequence with complementary nucleotides added to the template strand, and producing a transcript.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same dXMP where X is A, G, C, T or U within the first 9 nt, wherein the coding strand is modified to include 2 or fewer of the dXMP, where X is A, G, C, or T, within the first 9 nucleotides to improve the incorporation of 2'-fluoro-dXMP, where X is A, G, C or U, respectively, into the entire transcript, and producing a transcript. According to one aspect, the removable RNA element is a ribozyme. According to one aspect, the ribozyme and the added sequence is removed from the transcript.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same rXMP where X is A, G, C, T or U within the first 9 nt, altering the promoter sequence to include 2 or fewer of the same dXMP where X is A, G, C, T or U within the first 9 nt.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same dXMP where X is A, G, C, or T within the first 9 nt, wherein one or more dNMP is added to the coding strand after the promoter sequence with complementary nucleotides added to the template strand so that the coding strand is modified to include 2 or fewer of the dXMP (where X is A, G, C, or T) within the first 9 nt to facilitate the incorporation of 2'-fluoro-dXMP (where X is A, G, C, or U, respectively) into the entire transcript, and producing a transcript.

According to one aspect, a method of performing in vitro transcription is provided including combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U under conditions suitable for producing a transcript, wherein the double stranded nucleic acid includes a cyanophage Syn5 RNAP promoter sequence, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same dXMP where X is A, G, C, or T within the first 9 nt, wherein one or more dNMP coupled to a removable RNA element is added to the coding strand after the promoter sequence with complementary nucleotides added to the template strand so that the coding strand is modified to include 2 or fewer of the dXMP (where X is A, G, C, or T) within the first 9 nt to facilitate the incorporation of 2'-fluoro-dXMP (where X is A, G, C, or U, respectively) into the entire transcript, and producing a transcript.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIG. 1A depicts efficiency of 2'-F-dNMP incorporation by Syn5 RNA polymerase being correlated to the sequence at the 5' end of the RNA. Transcription reactions were carried out using Syn5 RNA polymerase on templates T1 (lanes 1-6), T2 (lanes 7-13), and T3 (lanes 14-20). In some reactions some of the four NTPs were replaced by the corresponding 2'-F analogs, as indicated at the top of the gel. The first twelve nucleotides at the 5'-end of the transcripts produced on each template are shown below each gel. The position of the migration of the DNA templates and the RNA products are marked on the left of the gel. FIG. 1B depicts efficiency of 2'-F-dNMP incorporation by Syn5 RNA polymerase on template T4. Normal NTPs were replaced by the corresponding 2'-F analogs as indicated at the top of each lane. The first twelve nucleotides at the 5'-end of the transcripts produced by template T4 are shown below each gel. The position of the migration of the DNA templates and the RNA products are marked on the left of the gel.

FIG. 2A to FIG. 2E are directed to the impact of initial sequence of transcript on the yield of transcripts synthesized by Syn5 RNA polymerase. FIG. 2A depicts the influence of different sequences at various positions in the first twelve nucleotides at the 5' end of transcripts on the yield of products synthesized by Syn5 RNA polymerase. The DNA template used in each reaction is indicated at the top of each lane. All of the templates were derived from template T4, from which the first twelve nucleotides at the 5' end of the RNA product are shown at the top of the gel. The variations in the sequence of RNA products from template T4 synthesized on each template are color coded; variations in the first three nucleotides are in orange, nucleotides four to six in blue, nucleotides seven to nine in purple, and nucleotides ten to twelve in green. The position of the migration of the DNA templates and the RNA products are marked on the left of the gel. FIG. 2B depicts influence of different sequences at various positions in the first ten nucleotides at the 5' end of transcripts on the yield of products synthesized by Syn5 and T7 RNA polymerases. Transcription reactions were carried out using Syn5 RNA polymerase (lanes 1-7, 13 and 14) and T7 RNA polymerase (lanes 8-12). The templates used for each reaction and the sequence of the first ten nucleotides at the 5' end of each RNA are shown at the bottom of the gel. Variations in RNA products encoded by each template are in blue background. FIG. 2C depicts influence of NTP concentration on the yield of products synthesized by Syn5 RNA polymerase. Transcription reactions were carried out on templates T32 (lanes 1-3), T2 (lanes 4-6) and T33 (lanes 7-9). The first three nucleotides of the transcript synthesized on each of these templates are UGA (T32), GGG (T2) and GGG (T33), as indicated at the bottom of the gel. The concentration of the NTP being varied in each reaction mixture is shown at the top; the concentrations of the other three NTPs were fixed at 4 mM. The position of the migration of the DNA templates and the RNA products are marked on the left of the gel. FIG. 2D and FIG. 2E depict incorporation of 2'-F-dCMP and/or 2'-F-dUMP into transcripts synthesized by Syn5 and T7 RNA polymerases. The templates used for each reaction (T18, T17, T28 and T4) and the sequence of the first twelve nucleotides at the 5' end of each RNA are shown at the bottom of the gel. The NTP analog present in each reaction is indicated at the top of the gel where "C/U" corresponds to reactions carried out in the presence of both 2'-F-dCTP and 2'-F-dUTP.

FIG. 3A depicts incorporation of 2'-F-dCMP and 2'-F-dUMP by Syn5 RNA polymerase in the presence of $Mg^{2+}$ or $Mn^{2+}$. Transcription reactions were carried out by Syn5 RNA polymerase on the template T1. The sequence of the first nine nucleotides of the 37 nt transcript produced on this template is shown at the bottom of the figure, with the C and U residues in grey background. The metal ion present in each reaction and its concentration are shown at the top of the gel. The reaction mixtures that contained both 2'-F-dCTP and 2'-F-dUTP (C/U) are also indicated. Lanes 1 contains only the DNA template as a marker. The position of the migration of the DNA templates and the RNA products are marked on the left of the gel. FIG. 3B depicts incorporation of 2'-F-dNMPs by Syn5 RNA polymerase in the presence of a mixture of $Mg^{2+}$ and $Mn^{2+}$ ions. Transcription reactions were carried out by Syn5 RNA polymerase on the template T1. The sequence of the first nine nucleotides of the 37 nt transcript produced on this template is shown at the bottom of the gel, with the C and U residues in grey background. FIG. 3C depicts incorporation of 2'-F-dNMPs into a 37 nt transcript and a 2,700 nt transcript by Syn5 RNA polymerase in the presence of a mixture of $Mg^{2+}$ and $Mn^{2+}$. Transcription reactions were carried out using either template T22, which encodes a 37 nt transcript (lanes 1-6), or T31, which encodes a 2,700 nt transcript (lanes 7 and 8). The sequence of the first nine nucleotides of each transcript is shown at the bottom of the gel, with the C and U residues in grey background. The metal ions present in each reaction and their concentrations are shown at the top of the gel; a mixture of 10 mM $Mg^{2+}$ and 5 mM $Mn^{2+}$ were present in the reaction mixtures in lanes 4-8. Also the reaction mixtures that contained both 2'-F-dCTP and 2'-F-dUTP or all four 2'-F-dNTPs are shown at the top of the gel. The position of the migration of the DNA templates and the RNA products are marked on the left of the gel.

FIG. 4A depicts incorporation of 2'-F-dNMPs into 37 nt and 2,700 nt transcripts using wild-type Syn5, Syn5-Y564F, and Syn5-Y574F RNA polymerases. Transcription reactions were carried out using either template T22, which encodes a 37 nt transcript (lanes 1-6), or T31, which encodes a 2,700 nt transcript (lanes 7-12). The sequence of the first nine nucleotides of each transcript is shown at the bottom of the gel, with the C and U residues in grey background. The RNA polymerase used for each reaction is indicated at the top of the gel. The reaction mixtures that contained only unmodified NTPs ("-") or both 2'-F-dCTP and 2'-F-dUTP ("C/U") are indicated at the top of the gel. $Mg^{2+}$ was used as the only metal ion in all reactions. The position of the migration of the DNA templates and the RNA products are marked on the left of the gel. FIG. 4B depicts incorporation of 2'-F-dNMPs by Syn5 and Syn5-Y564F RNA polymerases. Transcription reactions were carried out using template T8, which encodes a 37 nt transcript. Reactions were carried out using either wild-type Syn5 RNA polymerase (lanes 1-6) or Syn5-Y564F RNA polymerase (lanes 7-14). Each of the four NTPs was individually replaced by the corresponding 2'-F analog, as indicated at the top of the gel. In the reactions carried out in lanes 6 and 12, both CTP and UTP were replaced by 2'-F-dCTP and 2'-F-dUTP. In the reactions carried out in lanes 7 and 14, all four NTPs were replaced by 2'-F-dNTPs. The position of the migration of the DNA templates and the RNA products are marked on the left of the gel.

FIG. 8A depicts the internal Syn5 promoter in the Syn5 RNA polymerase gene being modified without changing the encoded amino acids, in order to abolish rolling-circle RNA synthesis that will deplete the NTP pool in E. coli cells when Syn5 RNA polymerase is expressed. FIG. 8B depicts E. coli cells harboring the modified vector growing much faster than those harboring the original vectors. FIG. 8C depicts the modified vector resulting in higher expression of Syn5 RNA polymerase without affecting its enzyme activity.

FIG. 9A and FIG. 9B are directed to Syn5-Y564F and Syn5-Y574F RNA polymerases. FIG. 9A depicts Syn5-Y564F and Syn5-Y574F RNA polymerases constructed based on sequence alignment (using CLC Sequence Viewer 6) to the region containing Y639 in T7 RNA polymerase. FIG. 9B depicts both mutant enzymes purified to homogeneity and analyzed by SDS-PAGE gel. The purified wild-type Syn5 RNA polymerase is shown on the left for comparison. Three concentrations (1, 2 and 4 µg) of each RNA polymerase were loaded into adjacent wells.

FIG. 10 is directed to the effect of $Mn^{2+}$ ions on 2'-F DNA synthesis by Syn5-Y564F RNA polymerase. Transcription reactions were carried out by Syn5-Y564F RNA polymerase. The metal ion present in each reaction and its concentration are shown at the top of the gel. All the reaction mixtures contained four 2'-F-dNTPs except for lane 13, which contained four rNTPs. Products of transcription reactions were separated by native gel electrophoresis and then stained with ethidium bromide. The position of the migration of the DNA templates and the transcripts are marked. The DNA template used is T30, which encodes a 2,700 nt transcript.

DETAILED DESCRIPTION OF CERTAIN EMBODIMENTS

Figure 1A:
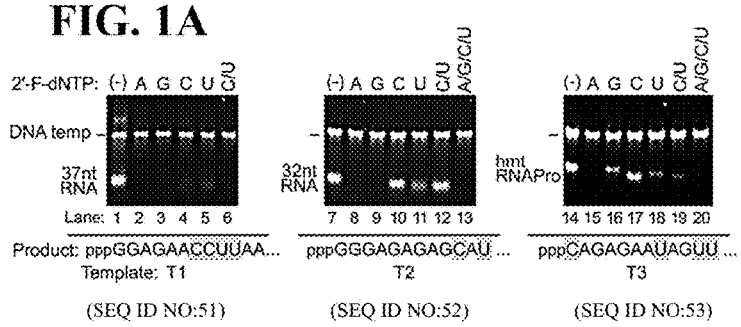
FIG. 1A and FIG. 1B are directed 2'-F-dNMP incorporation into transcripts synthesized by Syn5 RNA polymerase on various DNA templates. Products of transcription reactions were separated by native gel electrophoresis and then stained with ethidium bromide.

The subject application is directed in part to Syn5 RNAP, and to methods and mutants useful for making transcripts, such as transcripts including modified nucleotides. Methods described herein may be performed in vitro, ex vivo or in vivo, though the descriptions herein may be with respect to an in vitro method.

As used herein, the terms "nucleic acid molecule," "nucleic acid sequence," "nucleic acid fragment," "oligonucleotide," "oligonucleotide fragment" and "polynucleotide" are used interchangeably and are intended to include, but are not limited to, a polymeric form of nucleotides that may have various lengths, either deoxyribonucleotides or ribonucleotides, or analogs thereof. Nucleic acid molecules include single stranded DNA (ssDNA), double stranded DNA (dsDNA), single stranded RNA (ssRNA) and double stranded RNA (dsRNA). Different nucleic acid molecules may have different three-dimensional structures, and may perform various functions, known or unknown. Non-limiting examples of nucleic acid molecules include a gene, a gene fragment, a genomic gap, an exon, an intron, intergenic DNA (including, without limitation, heterochromatic DNA), messenger RNA (mRNA), transfer RNA, ribosomal RNA, ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers. Nucleic acid molecules useful in the methods described herein may comprise natural nucleic acid sequences and variants thereof, artificial nucleic acid sequences, or a combination of such sequences.

An oligonucleotide sequence refers to a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. An "oligonucleotide fragment" refers to an oligonucleotide sequence that has been cleaved into two or more smaller oligonucleotide sequences. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleotides, ribonucleotides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleotide, uridine, unless otherwise noted. Usually oligonucleotides comprise the four natural deoxynucleotides; however, they may also comprise ribonucleotides or non-natural or modified nucleotide analogs. It is clear to those skilled in the art when oligonucleotides having natural or non-natural nucleotides or modified nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning*, Second Edition (Cold Spring Harbor Laboratory, New York, 1989), and like references. Oligonucleotides and polynucleotides may be single stranded or double stranded.

Nucleic acid molecules may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 August 10(4):297-310. Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 April 10(2):117-21, Rusckowski et al. Antisense Nucleic Acid Drug Dev. 2000 October 10(5):333-45, Stein, Antisense Nucleic Acid Drug Dev. 2001 October 11(5): 317-25, Vorobjev et al. Antisense Nucleic Acid Drug Dev. 2001 April 11(2):77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

In certain exemplary embodiments, large polynucleotides are provided. In certain aspects, isolation techniques that maximize the lengths of polynucleotides (e.g., DNA molecules) obtained are used. For example, in situ lysis or deproteinization (e.g., with EDTA, detergent, protease, any combinations thereof and the like) after agarose embedding (as routinely performed for pulsed field gel electrophoresis) can be used to obtain polynucleotides.

Nucleic acid molecules may be isolated from natural sources or purchased from commercial sources. Oligonucleotide sequences may also be prepared by any suitable method, e.g., standard phosphoramidite methods such as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

Nucleic acid molecules may be obtained from one or more biological samples. As used herein, a "biological sample" may be a single cell or many cells. A biological sample may comprise a single cell type or a combination of two or more cell types. A biological sample further includes a collection of cells that perform a similar function such as those found, for example, in a tissue. Accordingly, certain aspects of the invention are directed to biological samples containing one or more tissues. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples.

In certain aspects, nucleic acid sequences expressed in, derived from or obtained from one or more organisms or host cells are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. As used herein, a "host cell" can be any cell derived or obtained from an organism. The terms "organism" and "host cell" further include, but are not limited to, a yeast (e.g., *S. cerevisiae*) cell, a yeast tetrad, a yeast colony, a bacterium, a bacterial colony, a virion, virosome, virus-like particle and/or cultures thereof, and the like.

In certain aspects, one or more biological samples are isolated from one or more subjects. As used herein, a "biological sample" may be a single cell or many cells. A biological sample may comprise a single cell type or a combination of two or more cell types. A biological sample further includes a collection of cells that perform a similar function such as those found, for example, in a tissue. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples. In certain aspects, a sample can be obtained from one or more of single cells in culture, metagenomic samples, embryonic stem cells, induced pluripotent stem cells, cancer samples, tissue sections, biopsies and the like, and any combinations of these.

In certain aspects of the invention, vectors and plasmids useful for transformation of a variety of host cells are provided. Vectors and plasmids are common and commercially available from companies such as Invitrogen Corp. (Carlsbad, Calif.), Stratagene (La Jolla, Calif.), New England Biolabs, Inc. (Beverly, Mass.) and Addgene (Cambridge, Mass.).

Certain aspects of the invention pertain to vectors, such as, for example, expression vectors. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, an exogenous nucleic acid described herein is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy on can be included such that a higher copy number can be obtained (e.g., pCC1FOS™, pCC2FOS™). Fosmid libraries are particularly useful for constructing stable libraries from complex genomes. Fosmids and fosmid library production kits are commercially available (EPICENTRE® Biotechnologies, Madison, Wis.). For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). It will be appreciated by those skilled in the art that the design of the expression vector can depend on such factors as the choice of the host cell to be transformed, the level of expression of protein desired, and the like.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells, a virion, a virosome, a virus-like particle, a parasitic microbe, an infectious protein and the like. Cells include eukaryotic cells such as yeast cells, plant cells, and animal cells. Particular cells include bacterial cells. Other suitable cells are known to those skilled in the art.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECT-ENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual*. 2nd, ed., Cold Spring harbor Laboratory, Cold Spring Harbor Laboratory Press, Cold Spring Harbor, N.Y., 1989), and other laboratory manuals.

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression in gram positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in gram negative bacteria (Scott et al., Plasmid 50(1):74-79 (2003)). Several plasmid derivatives of broad-host-range Inc P4 plasmid RSF1010 are also available with promoters that can function in a range of gram negative bacteria. Plasmid pAYC36 and pAYC37, have active promoters along with multiple cloning sites to allow for the heterologous gene expression in gram negative bacteria.

Chromosomal gene replacement tools are also widely available. For example, a thermosensitive variant of the broad-host-range replicon pWV101 has been modified to construct a plasmid pVE6002 which can be used to create gene replacement in a range of gram positive bacteria (Maguin et al., J. Bacteriol. 174(17):5633-5638 (1992)). Additionally, in vitro transposomes are available to create random mutations in a variety of genomes from commercial sources such as EPICENTRE® (Madison, Wis.).

Vectors useful for the transformation of *E. coli* are common and commercially available. For example, the desired genes may be isolated from various sources, cloned onto a modified pUC19 vector and transformed into *E. coli* host cells. Alternatively, the genes encoding a desired biosynthetic pathway may be divided into multiple operons, cloned into expression vectors, and transformed into various *E. coli* strains.

According to certain aspect of the invention, phages and their genetic material are provided. As used herein, the terms "phage" and "bacteriophage" are used interchangeably. Phage can be distinguished from each another based on their genetic composition and/or their virion morphology. Some phage have double stranded DNA genomes, including phage of the corticoviridae, lipothrixviridae, plasmaviridae, myrovridae, siphoviridae, sulfolobus shibate, podoviridae, tectiviridae and fuselloviridae families. Other phage have single stranded DNA genomes, including phage of the microviridae and inoviridae families. Other phage have RNA genomes, including phage of the leviviridae and cystoviridae families. Exemplary bacteriophage include, but are not limited to, Wphi, Mu, T1, T2, T3, T4, T5, T6, T7, P1, P2, P4, P22, fd, phi6, phi29, phiC31, phi80, phiX174, SP01, M13, MS2, PM2, SSV-1, L5, PRD1, Qbeta, lambda, UC-1, HK97, HK022 and the like.

Isolation, extraction or derivation of nucleic acid sequences may be carried out by any suitable method. Isolating nucleic acid sequences from a biological sample generally includes treating a biological sample in such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, $2^{nd}$ Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, $2^{nd}$ Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

Certain embodiments of the subject invention are directed to a first nucleic acid (e.g., a nucleic acid sequence encoding a Syn5 RNAP) or polypeptide sequence (e.g., a Syn5 RNAP) having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986) Nucl. Acids Res. 14:6745. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98%, or about 95%, about 96%, about 97%, about 98%, or about 99% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., Molecular Cloning: A Laboratory Manual, Second Edition, (1989) Cold Spring Harbor, N.Y.; Nucleic Acid Hybridization: A Practical Approach, editors B. D. Hames and S. J. Higgins, (1985) Oxford; Wash., D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

In certain exemplary embodiments, a polymerase of the subject invention (e.g., a cyanophage Syn5 RNAP) includes one or more protein tags. As used herein, the term "protein tag" refers to a heterologous polypeptide sequence linked to a polymerase of the invention. Protein tags include, but are not limited to, Avi tag (GLNDIFEAQKIEWHE) (SEQ ID NO:2), calmodulin tag (KRRWKKNFIAVSAANRFK-KISSSGAL) (SEQ ID NO:3), FLAG tag (DYKDDDDK) (SEQ ID NO:4), HA tag (YPYDVPDYA) (SEQ ID NO:5), His tag (HHHHHH) (SEQ ID NO:6), Myc tag (EQKLI-SEEDL) (SEQ ID NO:7), S tag (KETAAAKFERQHMDS) (SEQ ID NO:8), SBP tag (MDEKTTGWRGGHVVEG-LAGELEQLRARLEHHPQGQREP) (SEQ ID NO:9), Softag 1 (SLAELLNAGLGGS) (SEQ ID NO:10), Softag 3 (TQDPSRVG) (SEQ ID NO:11), V5 tag (GKPIPNPLL-GLDST) (SEQ ID NO:12), Xpress tag (DLYDDDDK) (SEQ ID NO:13), Isopeptag (TDKDMTITFTNKKDAE) (SEQ ID NO:14), SpyTag (AHIVMVDAYKPTK) (SEQ ID NO:15), and streptactin tag (Strep-tag II: WSHPQFEK) (SEQ ID NO:16).

Kits of the various components described herein are contemplated. As used herein, a "kit" refers to any delivery system for delivering materials or reagents for carrying out a method of the invention. In the context of assays, such delivery systems include systems that allow for the storage, transport, or delivery of reaction reagents (e.g., enzymes (e.g., a polymerase such as, for example, cyanophage Syn5 RNAP or a mutant thereof), nucleotides as known in the art and/or as described herein, modified nucleotides as known in the art and/or as described herein, 2'-F-dNTPs as known in the art and/or as described herein, etc., buffers, salts, source of $Mg^{+2}$, source of $Mn^{+2}$ etc. and any other reagents, chemicals, etc. as described herein, in the appropriate containers) and/or supporting materials (e.g., written instructions for performing the assay (e.g., in vitro transcription), etc.) from one location to another. For example, kits include one or more enclosures (e.g., boxes) containing the relevant reaction reagents and/or supporting materials for assays of the invention. Such contents may be delivered to the intended recipient together or separately. For example, a first container may contain an enzyme (e.g., enzymes (e.g., a polymerase such as, for example, cyanophage Syn5 RNAP or a mutant thereof)) for use in an assay, while a second container contains nucleotides, modified nucleotides, 2'-F-dNTPs, etc.

This invention is further illustrated by the following examples, which should not be construed as limiting. The contents of all references, patents and published patent applications cited throughout this application are hereby incorporated by reference in their entirety for all purposes.

Example I

Materials and Methods

Oligonucleotides were obtained from Integrated DNA Technology (oligonucleotides less than 60 nt were ordered at the 25 nmole scale and those longer than 60 nt were ordered at the 4 nmole Ultramer scale). DNA purification kits and Ni-NTA resin were obtained from Qiagen. Preparative Superdex 200 for gel filtration was obtained from GE Healthcare. Restriction endonucleases, T4 DNA ligase, Vent$_R$® DNA Polymerase, Q5® Site-Directed Mutagenesis Kit, T7 RNA polymerase, and *E. coli* inorganic pyrophosphatase were obtained from New England Biolabs. T7 R&DNA™ Polymerase (T7-Y639F RNA polymerase) was obtained from Epicentre. DNA Clean & Concentrator™-5 kit was obtained from ZYMO Research. RNaseOUT™ recombinant ribonuclease inhibitor was obtained from Invitrogen. NTPs were obtained from USB and 2'-F-dNTPs were obtained from Trilink.

Example II

Protein Expression and Purification

Figure 8A:
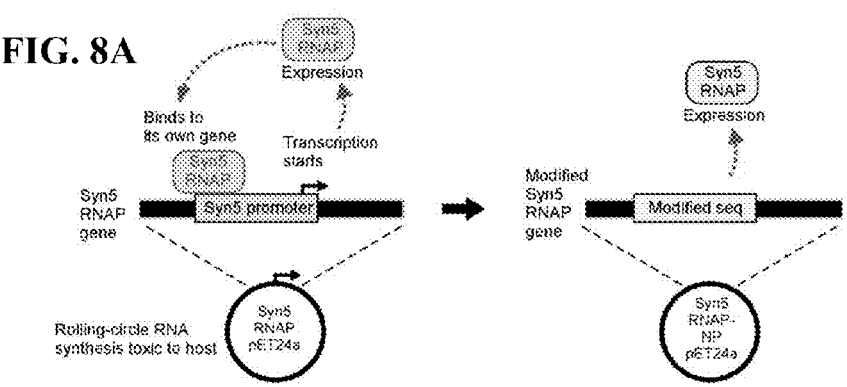
FIG. 8A to FIG. 8C are directed to a modified Syn5 RNA polymerase gene for improved expression in E. coli cells.
Figure 8B:
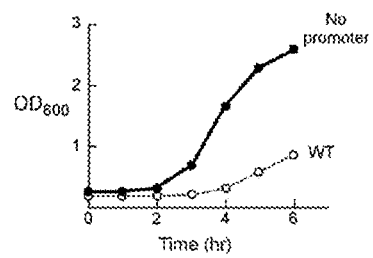
Figure 8C:
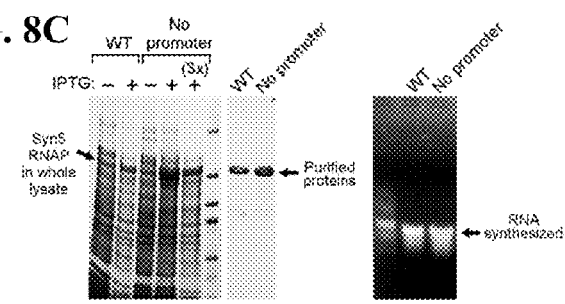

The expression vector described in Zhu, B., Tabor, S., Raytcheva, D. A., Hernandez, A., King, J. A. and Richardson, C. C. (2013) The RNA polymerase of marine cyanophage Syn5. *J. Biol. Chem.,* 288, 3545-3552 and Zhu, B., Tabor, S. and Richardson, C. C. (2014) Syn5 RNA polymerase synthesizes precise run-off RNA products. *Nucleic Acids Res.* 42, e33 each of which are hereby incorporated by reference in their entireties was modified to improve the expression of His-tagged Syn5 RNA polymerase by removing the internal Syn5 promoter sequence within the Syn5 RNA polymerase gene without changing the encoded amino acid as depicted in FIG. 8A. With this vector (Syn5 RNAP-NP-pET24), the synthesized Syn5 RNA polymerase will not initiate transcription from the internal promoter sequence, an event that would otherwise deplete the rNTP pools and inhibit the synthesis of the full-length mRNA for Syn5 RNA polymerase. *E. coli* cells harboring this vector grow significantly faster than those carrying the original plasmid and contain higher levels of overproduced protein as shown in FIG. 8B and FIG. 8C. Y564F and Y574F mutations were introduced into the Syn5 RNA polymerase gene in the Syn5 RNAP-NP-pET24 vector by PCR mutagenesis.

The purification procedure was modified from that previously described in Zhu, B., Tabor, S. and Richardson, C. C. (2014) Syn5 RNA polymerase synthesizes precise run-off RNA products. *Nucleic Acids Res.* 42, e33. *E. coli* BL21 (DE3) cells containing the plasmid Syn5 RNAP-NP-pET24 were grown in 2 L of LB medium containing 50 µg/ml kanamycin at 37° C. until they reached an OD$_{600}$ of 1.2. The gene for Syn5 RNA polymerase was induced by the addition of 0.5 mM IPTG at 25° C. and incubation was continued for 4-8 hr. The cells were harvested, resuspended in 50 mM sodium phosphate, pH 8.0, 100 mM NaCl, and lysed by three cycles of freeze-thaw in the presence of 0.5 mg/ml lysozyme. Solid NaCl was added to the lysed cells to a final concentration of 2 M and then the cleared lysate was collected after centrifugation. 5 ml Ni-NTA agarose was added to the clear lysate and gently mixed at 4° C. overnight. The resin was loaded and collected in a column and washed with 60 ml of Wash Buffer (50 mM sodium phosphate, pH 8.0, 2 M NaCl, and 10 mM imidazole). Syn5 RNA polymerase was eluted from the column using 30 ml Elution Buffer (50 mM sodium phosphate, pH 8.0, 2 M NaCl, and 100 mM imidazole). Eluted protein was concentrated to 1 ml using an Amicon Ultra-15 Centrifugal Filter Units (Millipore). The concentrated sample was loaded directly onto a 200 mL preparative Superdex 200 column. The gel filtration buffer contained 20 mM Tris-HCl pH 7.5, 2 M NaCl, 0.5 mM DTT, and 0.5 mM EDTA. Fractions were analyzed on SDS-PAGE gels and those fractions that contained homogenous Syn5 RNAP were pooled. The pooled fractions were concentrated by Amicon Ultra-15 Centrifugal Filter followed by dialysis against Dilution Buffer (50 mM Tris-HCl pH 8.0, 100 mM NaCl, 20 mM (β-ME, 1 mM EDTA, 50% glycerol, and 0.1% Triton® X-100) and stored at −20° C. Dilutions for enzyme assays were carried out using Dilution Buffer. The yield of Syn5 RNA polymerase following this procedure was greater than 20 mg protein per gram of wet cells, with the majority of the soluble Syn5 RNA polymerase (>80%) retained in the flow-through and wash fractions of the Ni-NTA step. Repetition of this procedure using the flow-through fraction of the Ni-NTA column generates similar amounts of purified protein. Syn5 RNA polymerase mutants Y564F and Y574F were purified following the same procedure resulting in a similar yield.

Example III

DNA Templates for Transcription Assays

DNA templates were constructed by annealing the complementary synthesized oligonucleotides listed below. Only the non-template strands are shown, listed 5'-3', with the promoters shown in bold and the nucleotides corresponding to residues 1 to 12 of the RNA products underlined.

T1:
(SEQ ID NO: 17)
GGTATTGGGCACCCGTAAGGAGAACCTTAAGGTT

TAACTTTAAGACCCTTAAGTG

T2:
(SEQ ID NO: 18)
GCCATTGGGCACCCGTAAGGGAGAGAGCATCGCT

TGGTGCAGATCGGGAC

T3
(template for human mitochondrial
tRNA$_{UGG}^{Pro}$):
(SEQ ID NO: 19)
GCCATTGGGCACCCGTAACAGAGAATAGTTTAAA

TTAGAATCTTAGCTTTGGGTGCTAATGGTGGAGT

TAAAGACTTTTTCTCTGACCA

T4:
(SEQ ID NO: 20)
GGTATTGGGCACCCGTAAGGAGAAGAAGAAGGTT

TAACTTTAAGACCCTTAAGTG

T5:
(SEQ ID NO: 21)
GGTATTGGGCACCCGTAAGGGGAAGAAGAAGGTT

TAACTTTAAGACCCTTAAGTG

T6:
(SEQ ID NO: 22)
GGTATTGGGCACCCGTAAGAAGAAGAAGAAGGTT

TAACTTTAAGACCCTTAAGTG

T7:
(SEQ ID NO: 23)
GGTATTGGGCACCCGTAAAGAGAAGAAGAAGGTT

TAACTTTAAGACCCTTAAGTG

T8:
(SEQ ID NO: 24)
GGTATTGGGCACCCGTAAGCAGAAGAAGAAGGTT

TAACTTTAAGACCCTTAAGTG

T9:
(SEQ ID NO: 25)
GGTATTGGGCACCCGTAAGGAAAAGAAGAAGGTT

TAACTTTAAGACCCTTAAGTG

T10:
(SEQ ID NO: 26)
GGTATTGGGCACCCGTAAGGATTTGAAGAAGGTT

TAACTTTAAGACCCTTAAGTG

T11:
(SEQ ID NO: 27)
GGTATTGGGCACCCGTAAGGACCCGAAGAAGGTT

TAACTTTAAGACCCTTAAGTG

T12:
(SEQ ID NO: 28)
GGTATTGGGCACCCGTAAGGAGAAAAAGAAGGTT

TAACTTTAAGACCCTTAAGTG

T13:
(SEQ ID NO: 29)
GGTATTGGGCACCCGTAAGGAGAAGCGGAAGGTT

TAACTTTAAGACCCTTAAGTG

T14:
(SEQ ID NO: 30)
GGTATTGGGCACCCGTAAGGAGAATTTGAAGGTT

TAACTTTAAGACCCTTAAGTG

T15:
(SEQ ID NO: 31)
GGTATTGGGCACCCGTAAGGAGAACCCGAAGGTT

TAACTTTAAGACCCTTAAGTG

T16:
(SEQ ID NO: 32)
GGTATTGGGCACCCGTAAGGAGAAGAAAAAGGTT

TAACTTTAAGACCCTTAAGTG

T17:
(SEQ ID NO: 33)
GGTATTGGGCACCCGTAAGGAGAAGAATTTGGTT

TAACTTTAAGACCCTTAAGTG

T18:
(SEQ ID NO: 34)
GGTATTGGGCACCCGTAAGGAGAAGAACCCGGTT

TAACTTTAAGACCCTTAAGTG

T19:
(SEQ ID NO: 35)
GGTATTGGGCACCCGTAAGGAGTAGAAGAAGGTT

TAACTTTAAGACCCTTAAGTG

T20:
(SEQ ID NO: 36)
GGTATTGGGCACCCGTAAGGAGTAGTAGAAGGTT

TAACTTTAAGACCCTTAAGTG

T21:
(SEQ ID NO: 37)
GGTATTGGGCACCCGTAAGGAGTTGAAGAAGGTT

TAACTTTAAGACCCTTAAGTG

T22:
(SEQ ID NO: 38)
GGTATTGGGCACCCGTAAGCAGAACCTTAAGGTT

TAACTTTAAGACCCTTAAGTG

T23:
(SEQ ID NO: 39)
GGTATTGGGCACCCGTAACAGGAACCTTAAGGTT

TAACTTTAAGACCCTTAAGTG

T24:
(SEQ ID NO: 40)
GGTTAATACGACTCACTATAGGAGAACCTTAAGG

TTTAACTTTAAGACCCTTAAGTG

T25:
(SEQ ID NO: 41)
GGTTAATACGACTCACTATAGGGGAACCTTAAGG

TTTAACTTTAAGACCCTTAAGTG

T26:
(SEQ ID NO: 42)
GGTTAATACGACTCACTATAGCAGAACCTTAAGG

TTTAACTTTAAGACCCTTAAGTG

T27:
(SEQ ID NO: 43)
GGTTAATACGACTCACTATACAGGAACCTTAAGG

TTTAACTTTAAGACCCTTAAGTG

T28:
(SEQ ID NO: 44)
GGTTAATACGACTCACTATAGGAGAAGAAGAAGG

TTTAACTTTAAGACCCTTAAGTG

T29:
(SEQ ID NO: 45)
TCCATTGGGCACCCGTAAGCAGGGAGGACGATGC

GGGCCTTCGTTTGTTTCGTCCACAGACGACTCGC

CCGA

T32:
(SEQ ID NO: 46)
GGTATTGGGCACCCGTAAUGAGAACCTTAAGGTT

TAACTTTAAGACCCTTAAGTG

T33:
(SEQ ID NO: 47)
ATTGGGCACCCGTAAGGGAGGACGATGCGGGCCT

TCGTTTGTTTCGTCCACAGACGACTCGCCCGA

Plasmid pUC19 with a single Syn5 promoter and 3 guanosine residues (5'-ATTGGGCACCCGTAAGGG-3') (SEQ ID NO:48) inserted between the BamHI and XbaI sites was linearized by NdeI to serve as template T30, which results in a 2,700 nt RNA. The first nine nucleotides of the RNA generated from this template (corresponding to an initiation sequence of nine nucleotides of the template strand) are GGGUCUAGA (SEQ ID NO:49). The linearized plasmid template T31 was derived from template T30 that was modified so that the first nine nucleotides of the RNA generated from this template (corresponding to an initiation sequence of nine nucleotides of the template strand) are GCAGAAGAA (SEQ ID NO:50). Linearized plasmids were purified with DNA Clean & Concentrator™-5 kit (ZYMO Research) prior to use in transcription assays.

Exemplary initiation sequences after the promoter sequence within the scope of the present disclosure that aid in the transcription of a nucleic acid sequence as described herein include G, GC, GCA, GCAG, GCAGA, GCAGAA, GCAGAAG, GCAGAAGA or GCAGAAGAA.

According to certain aspects of the present disclosure, methods are provided for altering the initiation sequence of a nucleic acid sequence to be transcribed to be one of G, GC, GCA, GCAG, GCAGA, GCAGAA, GCAGAAG, GCAGAAGA or GCAGAAGAA so as to facilitate transcription by Syn5 RNA polymerase or a Syn5 RNA polymerase mutant Y564F as described herein.

According to still further aspects, methods are provided for adding an initiation sequence of G, GC, GCA, GCAG, GCAGA, GCAGAA, GCAGAAG, GCAGAAGA or GCAGAAGAA to a nucleic acid sequence to be transcribed so as to facilitate transcription by Syn5 RNA polymerase or a Syn5 RNA polymerase mutant Y564F as described herein.

According to still further aspects, methods are provided for adding an initiation sequence of G, GC, GCA, GCAG, GCAGA, GCAGAA, GCAGAAG, GCAGAAGA or GCAGAAGAA coupled to a removable RNA element to a nucleic acid sequence to be transcribed so as to facilitate transcription by Syn5 RNA polymerase or a Syn5 RNA polymerase mutant Y564F as described herein. An exemplary RNA element includes a ribozyme. The ribozyme and the added initiation sequence in the transcript may be removed.

According to still further aspects, methods are provided for adding an initiation sequence of G, GC, GCA, GCAG, GCAGA, GCAGAA, GCAGAAG, GCAGAAGA or GCAGAAGAA to a nucleic acid sequence to be transcribed using 2-F-dNTP wherein the nucleic acid sequence has an initiation sequence including 3 or more of the same dXMP where X is A, G, C, T or U within the first 9 nucleotides, so as to facilitate transcription by Syn5 RNA polymerase or a Syn5 RNA polymerase mutant Y564F as described herein.

According to still further aspects, methods are provided for adding an initiation sequence of G, GC, GCA, GCAG, GCAGA, GCAGAA, GCAGAAG, GCAGAAGA or GCAGAAGAA coupled to a removable RNA element to a nucleic acid sequence to be transcribed using 2-F-dNTP wherein the nucleic acid sequence has an initiation sequence including 3 or more of the same dXMP where X is A, G, C, T or U within the first 9 nucleotides, so as to facilitate transcription by Syn5 RNA polymerase or a Syn5 RNA polymerase mutant Y564F as described herein. An exemplary RNA element includes a ribozyme. The ribozyme and the added initiation sequence in the transcript may be removed.

Example IV

Transcription Assays

Reaction conditions were those most commonly used for in vitro transcription reactions using T7 RNA polymerase. The reaction mixtures were analyzed on gels stained with ethidium bromide, which allowed for a direct comparison between the relative amount of RNA products and DNA templates. Reaction mixtures (10 µl) contained 40 mM Tris-HCl pH 8.0, 2 mM spermidine, 20 mM DTT, 20 mM $MgCl_2$ (or $MnCl_2$, or both, as specified), 4 mM of each of the 4 rNTPs (with 0 to 4 of the rNTPs replaced by their 2'-F-dNTP analogs), 1.5 U/µl RNaseOUT™ recombinant ribonuclease inhibitor, 0.006 U/µl E. coli inorganic pyrophosphatase, DNA template (2 µM annealed oligonucleotides (~200 ng/µl) or 20 nM linearized 2,700 by plasmid (~35 ng/µl)), and RNA polymerase (4 µM Syn5 RNAP polymerase or its Y564F mutant, or 5 U/µl T7 RNA polymerase from New England Biolabs or 5 U/µl T7-Y639F RNA polymerase (T7 R&DNA™ Polymerase) from Epicentre). Reaction mixtures were incubated at 37° C. for 4 hrs (8 hrs for assays described in FIG. 5C and FIG. 6 lower gels). 1 µl of the mixtures were mixed with 7 µl $H_2O$ and 7 µl denaturing RNA loading dye (New England Biolabs). Samples (5 µl was used for loading onto all gels except those shown in FIG. 1B and FIG. 2A, which used 2.5 µl) were then loaded onto 10% TBE native gels (Bio-Rad) or 2% TAE agarose gels (for the 2,700 nt RNA). DNA templates and RNA products were separated by electrophoresis and visualized by staining with ethidium bromide. Transcription yield shown in Table 1 was calculated based on comparison of the intensity of the product band to that of the DNA template band. To confirm the yield of some reactions, one unit of DNase I (New England Biolabs) was added to each reaction mixture and incubated for an additional 20 min at 37° C. to remove the DNA templates. The transcripts were then purified serially with phenol/chloroform extraction, Micro Bio-Spin™ P-30 Gel Columns (RNase-free, Bio-Rad), and ethanol precipitation. The amount of purified transcript was determined using NanoPhotometer® (Implen).

Example V

Influence of Initiation Sequences on 2'-F-dNMP Incorporation and Transcription Yield by Syn5 RNA Polymerase 2'-F-dCMP and 2'-F-dUMP were incorporated into small RNAs (<100 nt), such as for use as siRNA, RNA aptamers, and ribozymes. The ability of wild-type Syn5 RNA polymerase to incorporate 2'-F-dNMPs into RNA was examined. Syn5 RNA polymerase exhibits dramatically different abilities to incorporate each of the four different 2'-F-dNMPs into three different DNA templates that encode a 37 nt RNA, a 32 nt RNA, and a tRNA as shown in FIG. 1A. In general, 2'-F-dCMP is incorporated much more efficiently than the other three analogs. Based on the sequences of these three templates, the efficiency of 2'-F-dNMP incorporation by Syn5 RNA polymerase is affected by the first 9 nucleotides of the initiation sequence (i.e. the first 12 nucleotides) of the RNAs synthesized. Accordingly, methods are provided for transcription using Syn5 RNAP or a mutant thereof under conditions described herein where the transcription initiation sequence is as described herein. Accordingly, methods are provided for transcription using Syn5 RNAP or a mutant thereof under conditions described herein where the transcript includes one or more of 2'-F-dCMP, 2'-F-dUMP, 2'-F-dAMP and 2'-F-dGMP. According to one aspect, methods are provided for transcription using Syn5 RNAP or a mutant thereof under conditions described herein where each nucleotide of the transcript is 2'-F-dNMP, where 2'-F-dNMP is one of 2'-F-dCMP, 2'-F-dUMP, 2'-F-dAMP and 2'-F-dGMP.

On template T2, where there is only one C or U in the initiation region, 2'-F-dCMP or 2'-F-dUMP or both can be incorporated efficiently into the full-length transcript (FIG. 1A, lanes 10-12). In contrast, on template T1, where all four bases are present multiple times adjacent to one another, none of the 2'-F analogs can be efficiently incorporated into the full-length transcript (FIG. 1A, lanes 1-6). Template T3, that encodes one C in the initiation region as the initiating nucleotide, allows efficient incorporation of 2'-F-dCMP as the 5' nucleotide (FIG. 1A, lane 17). Although this template has multiple G's and U's, they are distal to the 5' end, so that they have less of an inhibitory effect on the incorporation of 2'-F-dGMP and 2'-F-dUMP, respectively (FIG. 1A, lanes 16 and 18).

Figure 1B:
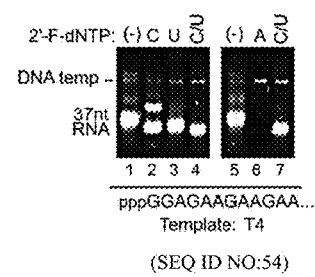

Template (T4) is the same as T1 except that C7C8U9U10 (numbers represent the position of the nucleotide in RNA counting from the 5'-end) was replaced by G7A8A9G10. We examined the ability of Syn5 RNA polymerase to initiate transcription on this template in the presence of 2'-F-dNTPs (FIG. 1B). Template T4 has no C or U in the initiation region, resulting in very efficient incorporation of both 2'-F-dCMP and 2'-F-dUMP, with the total amount of transcript produced being at least 50% of that produced in the absence of any analogs (FIG. 1B, compare lanes 1 and 4, 5 and 7; Table 1). As expected, there is no transcription of this template in the presence of 2'-F-dATP (FIG. 1B, lane 6) due to the presence of more than one A in the first 9 nucleotides of the template. Accordingly, methods are provided for incorporating a particular 2'-F-dNTP where N is G, A, C or U into an RNA by using a coding sequence which lacks or has fewer than two of the particular nucleotide in the first 9 nucleotides.

When comparing T1 and T4 as templates for run-off transcription with Syn5 RNA polymerase, the incorporation of 2'-F-dCMP and 2'-F-dUMP, and also the overall yield of transcripts in the absence of any analogs, are different. When C7C8U9U10 in T1 is replaced by G7A8A9G10 in T4, the yield increases 10 fold (FIG. 1A, lane 1 vs. FIG. 1B, lane 1; FIG. 2B, lane 1 vs. lane 5; Table 1). This difference was unexpected since previous studies with T7 RNA polymerase suggested that this region did not have a significant effect on transcription. See Milligan, J. F., Groebe, D. R., Witherell, G. W. and Uhlenbeck, O. C. (1987) Oligoribonucleotide synthesis using T7 RNA polymerase and synthetic DNA templates. *Nucleic Acids Res.*, 15, 8783-8798 hereby incorporated by reference in its entirety.

The effect of various sequences in the 1-12 nt region on the yield of transcription products using Syn5 RNA polymerase were tested using 28 different templates (FIGS. 2A and 2B). These templates are divided into four groups, each focusing on a different 3 nt region. Multiple product bands are observed in some lanes when the RNA is overloaded; reducing the amount of product loaded onto these gels results in bands with greater uniformity (for example, compare the sample loaded in FIG. 2B, lane 1, with the identical sample loaded at half the concentration in FIG. 2A, lane 1). Without wishing to be bound by scientific theory, it may be that the multiple bands observed at high concentrations of RNA represent different secondary structures in the same RNA product.

Tests were conducted to determine transcription using Syn5 RNAP and different sequences corresponding to nts 1-3 in the RNA. Efficient transcription resulted using a variety of sequences such as G1G2A3, G1A2A3, A1G2A3, G1C2A3, and C1A2G3 (FIG. 2A, lanes 1 and 3-5; FIG. 2B, lanes 5-7), with the highest yield observed using G1C2A3 (FIG. 2A, lane 5 vs. 1-4; FIG. 2B, lane 6 vs. 5 and 7). This result is consistent with the fact that in the cyanophage Syn5 genome, the sequence G1C2A3 is found following both of the promoters. The trinucleotide template sequence that provides for the greatest amount of transcription with T7 RNA polymerase (G1G2G3) supports the lowest yield by Syn5 RNA polymerase (FIG. 2A, lane 2). Transcription by T7 RNA polymerase on templates with various sequences at the first three nucleotide positions of the transcript was examined. G1G2G3 supports the highest yield (FIG. 2B, lane 9), and G1G2A3 and G1C2A3 work efficiently (FIG. 2B, lanes 8 and 10), while with the template C1A2G3, transcription by T7 RNA polymerase is much less efficient compared to Syn5 RNA polymerase (FIG. 2B, lane 11 vs. 7).

For template sequences corresponding to the regions 4-6 and 7-9 of the transcript, a consecutive stretch of three A's or U's in either of these regions of the transcript is very inhibitory to Syn5 RNA polymerase (FIG. 2A, lanes 6 and 9, 7 and 11). The sequences of template T9 and T12 include a consecutive stretch of four (T9) and five (T12) A's in the initiation region. Since multiple and often consecutive A's are present in most templates that are transcribed efficiently, three consecutive A's in the initiation region may be inhibitory to Syn5 RNA polymerase.

Three consecutive U's in Templates T10 and T14 result in poor synthesis. The effect of multiple U's at different positions in the initiation region was examined. When one U was introduced into the product of template T4 at position 5 (T19), the yield decreased about 3-fold (FIG. 2B, lane 2 vs. 1); an additional U in this region, whether at position 8 (T20) or 6 (T21), further decreased the yield by at least 20-fold (FIG. 2B, lanes 3 and 4 vs. 1). Other sequences, such as C7C8C9 and G7C8G9, also reduce the yield of transcripts produced by Syn5 RNA polymerase, but in these cases the amount of product was still substantial (FIG. 2A, lanes 10 and 12). In the template region corresponding to nucleotides 10-12, all substitutions, including A10A11A12, U10U11U12 and C10C11C12, have minimal effect on the yield (FIG. 2A, lanes 13-15 vs. 1).

Accordingly, more than two U's in the first nine nucleotides of the RNA product has a negative effect on transcription by Syn5 RNA polymerase.

The plasmid template (T30) was derived from plasmid pUC19 and encodes for an RNA transcript that starts with GGGUCUAGA. Based on the results just discussed, this sequence should be an inefficient template for Syn5 RNA polymerase, both because it starts with three consecutive G's, and there are two U's in the first nine nucleotides. Template (T31) is the sequence of T30 except the sequence of the first nine nucleotides of the transcript, "GGGUC-UAGA", was replaced by the sequence "GCAGAAGAA". The yield of transcripts synthesized by Syn5 RNA polymerase on this template is more than 100-fold greater than that produced using the original template, approaching ~70 μg of RNA synthesized per 10 μl reaction (FIG. 2B, compare lanes 14 and 13; Table 1).

Figure 2C:
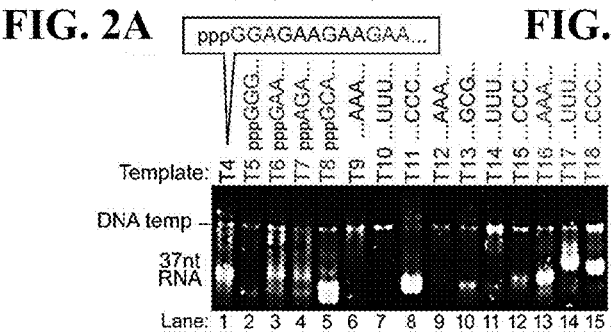
Figure 2C:
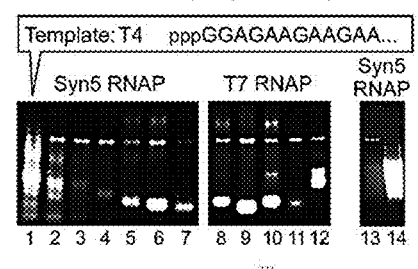
Figure 2C:
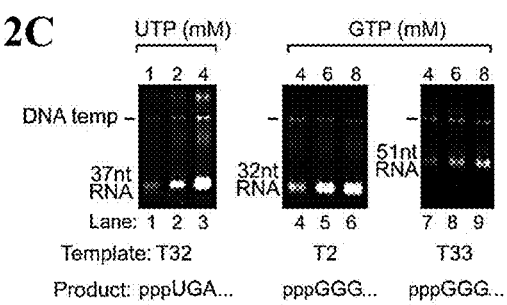

Transcription by Syn5 RNA polymerase that starts with U is very inefficient using 0.2 mM UTP. Increasing the concentration of UTP increases the yield of RNA produced by Syn5 RNA polymerase. When the reaction is carried out using 4 mM UTP, transcription is increased (FIG. 2C, lane 1-3). Similarly, while transcription by Syn5 RNA polymerase that starts with GGG is very inefficient using 4 mM GTP, increasing the concentration of GTP to 8 mM significantly increases the amount of transcript synthesized (FIG. 2C, lanes 4-9). With current reaction conditions, there is no limitation on the sequence of the first three positions of the transcripts produced using Syn5 RNA polymerase. In contrast, tests carried out increasing the concentration of UTP in the reaction mixture showed little effect on improving the yield of RNAs that contain more than two U's in nucleotides 1 to 9 of the transcript. Accordingly, useful transcription templates for use by Syn5 RNA polymerase lack more than two U's in nucleotides 1 to 9 of the transcript.

Replacement of C7C8U9U10 by G7A8A9G10 increases the yield of transcripts produced by Syn5 RNA polymerase by a factor of ten (FIG. 2B, compare lanes 5 and 1). In contrast, this change only slightly increases the yield of transcripts using T7 RNA polymerase (FIG. 2B, lane 12 vs. 8). This result again demonstrates that each of these RNA polymerases have distinct sequence preferences for the RNA transcribed near the start of the transcripts.

Figure 2D:
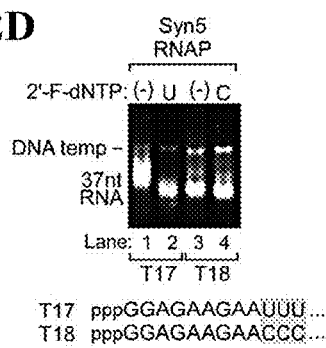

Just as the sequence of the region corresponding to residues 10 to 12 of the transcript has little effect on the yield of transcripts produced by Syn5 RNA polymerase, the sequence of this region also has negligible effect on the incorporation of 2'-F-dNMPs (FIG. 2D). On template T17, that encodes for an RNA transcript with U10U11U12, Syn5 RNA polymerase can efficiently incorporate 2'-F-dUMP, with at most a three-fold reduction in the amount of transcripts (FIG. 2D, compare lanes 1 and 2). Transcription by Syn5 RNA polymerase on template T18, which encodes an RNA transcript with C10C11C12, the yield of transcripts is comparable using either CTP or 2'-F-dCTP (FIG. 2D, lanes 3 and 4).

The efficiency of incorporation of 2'-F-dUMP and 2'-F-dCMP into transcripts using Syn5 RNA polymerase will depend on the sequence of the first nine nucleotides of the transcript: if the RNA transcript has less than two C's or U's in the first nine nucleotides, then Syn5 RNA polymerase will efficiently incorporate these analogs using the standard conditions described herein.

Figure 2E:
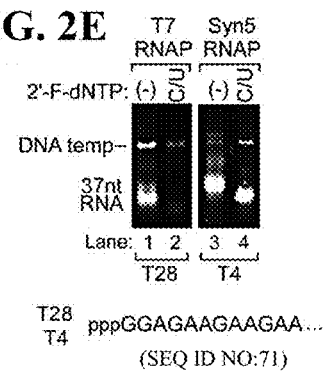

Tests determining incorporation of 2'-F-dCMP and 2'-F-dUMP using T7 RNA polymerase were carried out. A DNA template T28 was constructed that encodes the same RNA as that encoded by template T4 for Syn5 RNA polymerase (lacking any C's or U's in the first nine nucleotides). On this template, 2'-F-dCTP and 2'-F-dUTP inhibit the amount of transcripts produced by T7 RNA polymerase, at least by a factor of ten (FIG. 2E, compare lanes 2 and 1). This result is in dramatic contrast to the minimal effect that these analogs have on transcription by Syn5 RNA polymerase (FIG. 2E, compare lanes 4 and 3).

Example VI

Effect of Manganese Ions on the Incorporation of 2'-F-dNMPs by Syn5 RNA Polymerase Templates encoding multiple C's and U's in the initiation region (nucleotides 1-9) are not transcribed efficiently by Syn5 RNA polymerase in the presence of 2'-F-dCTP and 2'-F-dUTP using the standard conditions described above. Accordingly, reaction conditions were varied in order to optimize transcription on these templates. Manganese ions decrease the substrate discrimination for many polymerases. See Tabor, S. and Richardson, C. C. (1989) Effect of manganese ions on the incorporation of dideoxynucleotides by bacteriophage T7 DNA polymerase and *Escherichia coli* DNA polymerase I. *Proc. Natl. Acad. Sci. U.S.A.*, 86, 4076-4080. T7 RNA polymerase can use $Mn^{2+}$ instead of $Mg^{2+}$ for catalysis; the optimum concentration of $Mn^{2+}$ is 2.0-2.5 mM, ten fold lower than the optimum concentration of $Mg^{2+}$. See Gopalakrishna, S., Gusti, V., Nair, S., Sahar, S. and Gaur, R. K. (2004) Template-dependent incorporation of 8-N3AMP into RNA with bacteriophage T7 polymerase. *RNA*, 10, 1820-1830. However, even at the optimum metal concentrations, the activity of T7 RNA polymerase with $Mn^{2+}$ is much lower than that with $Mg^{2+}$. See Sousa R. and Padilla R. (1995) A mutant T7 RNA polymerase as a DNA polymerase. *EMBO J.*, 14, 4609-4621.

A mixture of $Mn^{2+}$ and $Mg^{2+}$ ions has been used successfully to provide the two metal ions required for catalysis in the T7 RNA polymerase active site. See Steitz, T. A. (2009) The structural changes of T7 RNA polymerase from transcription initiation to elongation. *Curr. Opin. Struct. Biol.*, 19, 683-690; Gopalakrishna, S., Gusti, V., Nair, S., Sahar, S. and Gaur, R. K. (2004) Template-dependent incorporation of 8-N3AMP into RNA with bacteriophage T7 RNA polymerase. *RNA*, 10, 1820-1830; and Afonin, K. A., Kireev a, M., Grabow, W. W., Kashlev, M., Jaeger, L. and Shapiro, B. A. (2012) Co-transcriptional assembly of chemically modified RNA nanoparticles functionalized with siRNAs. *Nano Lett.*, 12, 5192-5195. Presumably, some T7 RNA polymerase molecules will have one $Mn^{2+}$ and one $Mg^{2+}$ in their active sites, resulting in relaxed specificity for substrate analogs. However, since concentrations of $Mn^{2+}$ ions greater than 2.5 mM are highly inhibitory to T7 RNA polymerase, the concentration of $Mg^{2+}$ ions in these mixtures must also be reduced to levels that are suboptimal for T7 RNA polymerase activity.

Figure 3A:
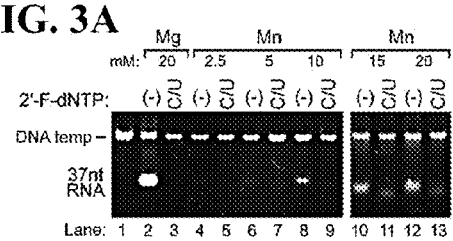
FIG. 3A to FIG. 3C are directed to the effect of $Mn^{2+}$ ions on 2'-F-dNMP incorporation by Syn5 RNA polymerase. Products of transcription reactions were separated by native gel electrophoresis and then stained with ethidium bromide.
Figure 3B:
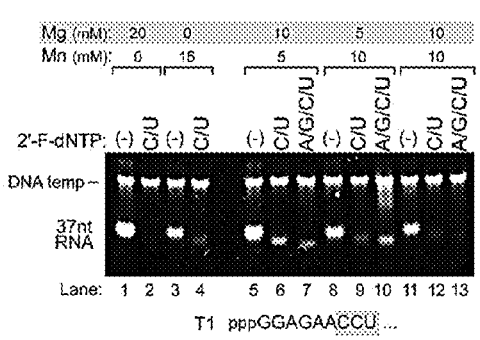

The natural hosts of cyanophage Syn5 are ocean-dwelling cyanobacteria. In this environment, the intracellular concentration of $Mn^{2+}$ is 100 times the concentration found in *E. coli*, the natural host for bacteriophage T7. See Keren, N., Kidd, M. J., Penner-Hahn, J. E. and Pakrasi, H. B. (2002) A light-dependent mechanism for massive accumulation of manganese in the photosynthetic bacterium *Synechocystis* sp. PCC 6803. *Biochemistry*, 41, 15085-15092; and Imashimizu, M., Tanaka, K. and Shimamoto, N. (2011) Comparative Study of cyanobacterial and *E. coli* RNA polymerases: misincorporation, abortive transcription, and dependence on divalent cations. *Genet. Res. Int.* 2011, 572689. It was therefore investigated whether Syn5 RNA polymerase will retain activity at higher $Mn^{2+}$ concentrations than will T7 RNA polymerase. Under standard reaction conditions, the optimum $Mn^{2+}$ concentration for Syn5 RNA polymerase activity is 15-20 mM (FIG. 3A), which is similar to its optimum $Mg^{2+}$ concentration. The yield of transcripts produced in the presence of the optimum concentration of $Mn^{2+}$ is several-fold lower than that produced at the optimum concentration of $Mg^{2+}$ (FIG. 3A, lane 12 vs. lane 2). However, the incorporation of 2'-F-dCMP and 2'-F-dUMP by Syn5 RNA polymerase is more efficient in the presence of 15 mM $Mn^{2+}$ than in the presence of 20 mM $Mg^{2+}$ (FIG. 3A, lane 11 vs. lane 3). Since the optimal concentrations for each metal ion in Syn5 transcription reactions are similar, both ions can be present together in the Syn5 transcription reaction at high concentrations. With the combination of 10 mM $Mg^{2+}$ and 5 mM $Mn^{2+}$, the yield of transcripts produced using all natural NTPs is within 50% of that observed in the presence of only 20 mM $Mg^{2+}$ (FIG. 3B, compare lanes 5 and lane 1). Under these conditions, using a mixture of the two metal ions, the incorporation of 2'-F-dCMP and 2'-F-dUMP is substantially improved compared to reactions that contain only 15 mM $Mn^{2+}$ (FIG. 3B, compare lanes 6 and 4). Thus this combination of the two metal ions provides a high yield of transcripts and low discrimination against 2'-F-dCTP and 2'-F-dUTP. Accordingly, methods are provided for transcription using Syn5 RNAP or a mutant thereof under conditions described herein where the $Mg^{2+}$ and $Mn^{2+}$ are used singly or in combination in the amounts described herein.

Figure 3C:
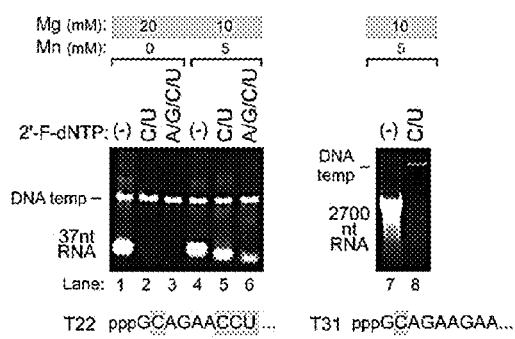

In the presence of all four 2'-F-dNTPs, Syn5 RNA polymerase synthesizes a significant amount of products containing the complete substitution of 2'-fluoro analogs, either in the presence of 10 mM $Mg^{2+}$ and 5 mM $Mn^{2+}$ or 5 mM $Mg^{2+}$ and 10 mM $Mn^{2+}$ (FIG. 3B, lanes 7 and 10). The highest amount of transcripts containing all four 2'-F-dNMPs are observed when the first three nucleotides of the product are the preferred sequence GCA (template T22 in FIG. 3C) and the metal mixture consists of 10 mM $Mg^{2+}$ and 5 mM $Mn^{2+}$. Under these conditions, the yield of product containing all four 2'-F-dNMPs is about 10-fold lower than that produced using natural NTPs (FIG. 3C, compare lanes 6 and 4) and four-fold lower than transcripts containing only 2'-F-dCMP and 2'-F-dUMP analogs (FIG. 3C, compare lanes 5 and 4). In these examples, the templates contains multiple C's in the first nine nucleotides of the transcript, so under standard reaction conditions the Syn5 RNA polymerase does not yield any product (FIG. 3B lane 2; FIG. 3C lanes 2 and 3). The use of a high concentration of both $Mg^{2+}$ and $Mn^{2+}$ improves dramatically the yield of transcripts produced by wild-type Syn5 RNA polymerase with 2'-F-dNTPs. Accordingly, methods are provided for transcription using Syn5 RNAP or a mutant thereof under conditions described herein where the transcript includes one or more of 2'-F-dCMP, 2'-F-dUMP, 2'-F-dAMP and 2'-F-dGMP. According to one aspect, methods are provided for transcription using Syn5 RNAP or a mutant thereof under conditions described herein where each nucleotide of the transcript is 2'-F-dNMP, where 2'-F-dNMP is one of 2'-F-dCMP, 2'-F-dUMP, 2'-F-dAMP and 2'-F-dGMP.

Example VII

Effect of Y564F and Y574F Mutations on 2'-F-dNMP Incorporation by Syn5 RNA Polymerase Although Syn5 RNA polymerase efficiently produces small 2'-F RNAs and also 2'-F DNAs in the presence of a high concentration of $Mg^{2+}$ and $Mn^{2+}$, the synthesis of long 2'-F RNAs is poor (FIG. 3C). For example, Syn5 RNA polymerase synthesizes a large amount of a 2,700 nt RNA with the four natural rNTPs (FIG. 3C, lane 7), whereas the amount of product synthesized when 2'-F-dCTP and 2'-F-dUTP are substituted for CTP and UTP is barely detectable (FIG. 3C, lane 8). In order to improve the efficiency of the production of long 2'-F RNAs, the effect of genetic alterations in the Syn5 RNA polymerase was analyzed. A T7 RNA polymerase with the tyrosine at residue 639 replaced by phenylalanine (Y639F) improves the efficiency with which T7 RNA polymerase incorporates nucleotide analogs. See Sousa R. and Padilla R. (1995) A mutant T7 RNA polymerase as a DNA polymerase. *EMBO J.*, 14, 4609-4621. It is to be understood that one of skill will understand that the difference between 2'-F RNA and 2'-F DNA will depend upon the number of nucleotides replaced by their corresponding 2'-F-dNMP analog.

Two tyrosine residues, Y564 and Y574 of Syn5 RNA polymerase, were identified in a location that potentially could alter the recognition of the nucleoside 2'-group by the polymerase (FIG. 9A). Two Syn5 RNA polymerases were constructed that harbor either a Y564F (Syn5-Y564 RNA polymerase) or Y574F (Syn5-Y574F RNA polymerase) alteration, and purified each of the overproduced enzymes to homogeneity, using the procedures described for the wild-type Syn5 RNA polymerase. In both cases, the same high yield was obtained as that obtained for the wild-type protein (FIG. 9B).

Figure 4A:
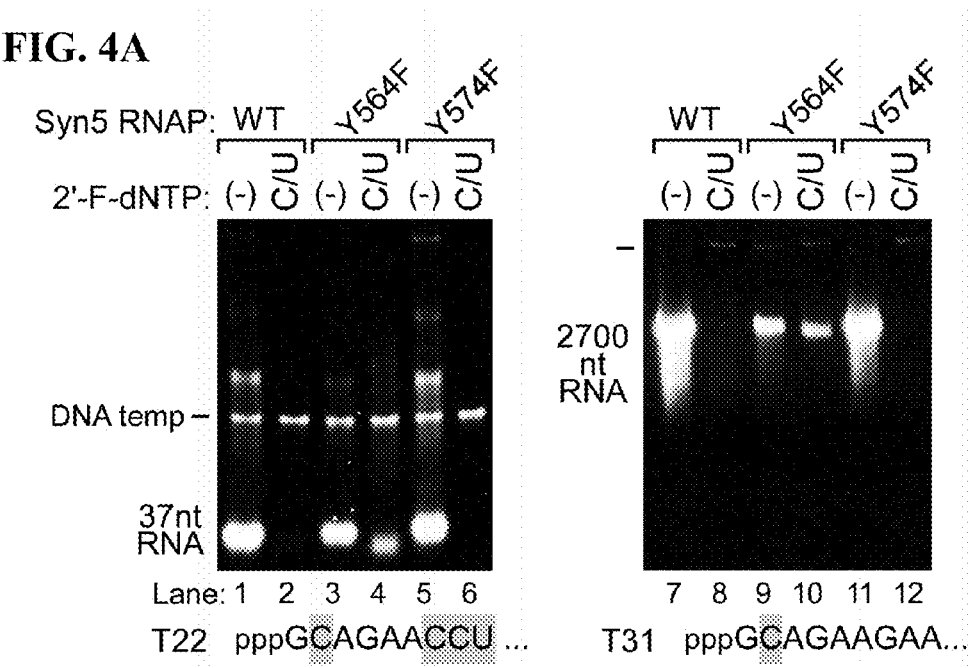
FIG. 4A and FIG. 4B are directed to incorporation of 2'-F-dNMPs by wild-type, Y564F, and Y574F Syn5 RNA polymerases. Products of transcription reactions were separated by native gel electrophoresis and then stained with ethidium bromide.

The ability of the two altered Syn5 RNA polymerases to synthesize transcripts containing 2'-F-dCMP and 2'-F-dUMP was examined. Syn5-Y574F RNA polymerase behaves similar to wild-type Syn5 RNA polymerase with regard to the ability to incorporate 2'-F-dCMP and 2'-F-dUMP (FIG. 4A lanes 1, 2, 5-8, 11 and 12). Syn5-Y564F RNA polymerase, on the other hand, synthesizes 2'-F-RNA much more efficiently than does wild-type Syn5 RNA polymerase. In the presence of 2'-F-dCTP and 2'-F-dUTP, the amount of transcript produced is 30% of that observed with CTP and UTP on templates producing both a 37 nt RNA and a 2,700 nt RNA (FIG. 4A lanes 3, 4, 9 and 10). The overall yield of RNA produced with this mutant RNA polymerase is reduced compared to wild-type Syn5 RNA polymerase (FIG. 4A lane 3 vs. 1 and lane 9 vs. 7). Nevertheless, the yield of RNA's containing 2'-F-dCMP and 2'F-dUMP produced by Syn5-Y564F RNA polymerase can reach 0.4 µg/µl reaction for a 37 nt RNA and 1 µg/µl reaction for a 2,700 nt RNA (FIG. 4A, lanes 4 and 10).

Figure 4B:
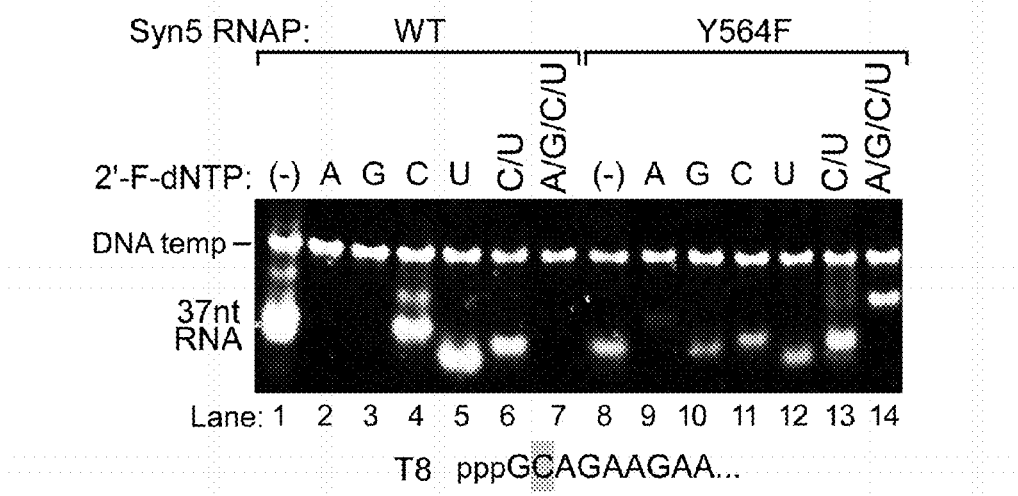

On a template encoding an RNA lacking U and with only one C in the initiation region (T8), wild-type Syn5 RNA polymerase efficiently incorporates 2'-F-dCMP and 2'-F-dUMP (FIG. 4B, lanes 4-6), while no incorporation is observed using 2'-F-dATP or 2'-F-dGTP (FIG. 4B, lanes 2 and 3). Syn5-Y564F RNA polymerase, however, can synthesize transcripts that contain all four 2'-F-dNMPs (FIG. 4B, lane 9-12), albeit with varying efficiencies. Using this template, the Syn5-Y564F RNA polymerase synthesizes a 37 nt RNA with complete replacement of NMPs by 2'-F-dNMPs at a yield of 0.1 µg/µl reaction (FIG. 4B, lane 14). Accordingly, methods are provided for transcription using Syn5 RNAP or a mutant thereof under conditions described herein where the transcript includes one or more of 2'-F-dCMP, 2'-F-dUMP, 2'-F-dAMP and 2'-F-dGMP. According to one aspect, methods are provided for transcription using Syn5 RNAP or a mutant thereof under conditions described herein where each nucleotide of the transcript is 2'-F-dNMP, where 2'-F-dNMP is one of 2'-F-dCMP, 2'-F-dUMP, 2'-F-dAMP and 2'-F-dGMP.

Example VIII

Synthesis of 2'-F RNAs (2'-F DNAs) with Syn5 RNA Polymerases

Figure 5:
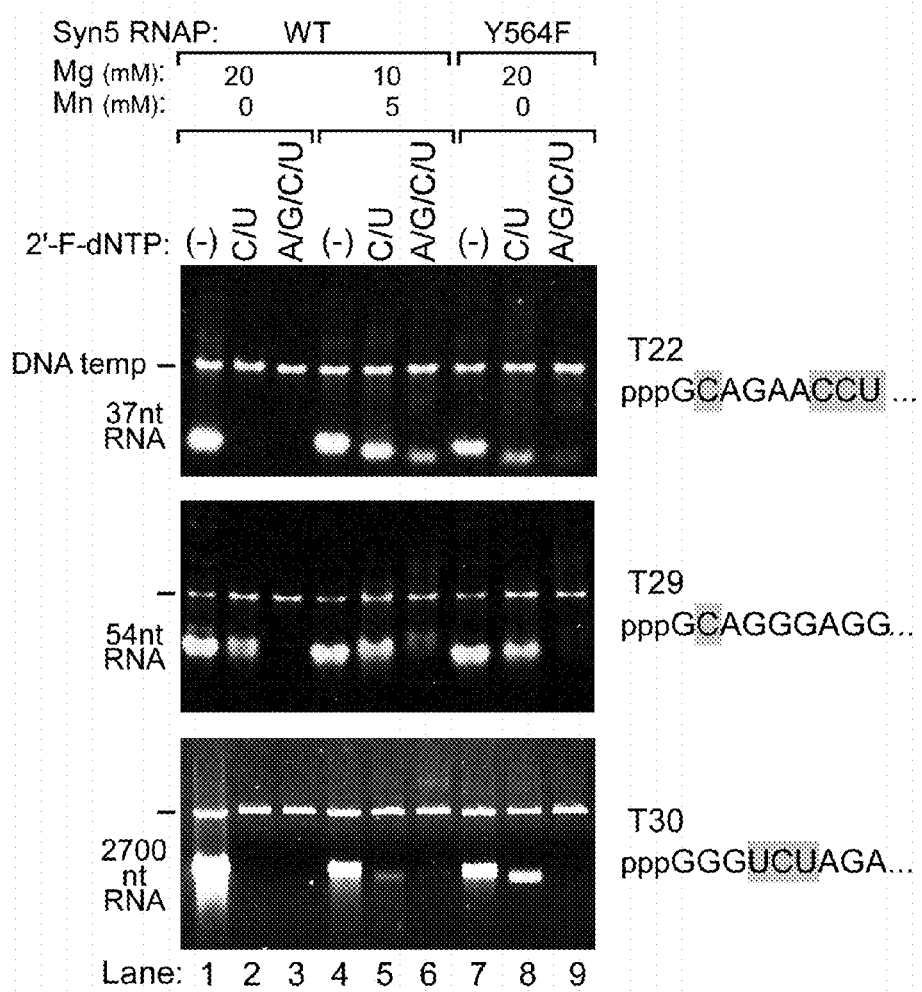
FIG. 5 is directed to synthesis of 2'-F RNAs by wild-type and Y564F Syn5 RNA polymerases on three different templates. Transcription reactions were carried out using either wild-type Syn5 RNA polymerase (lanes 1-6) or Syn5-Y564F RNA polymerase (lanes 7-9). Reactions were carried out in the presence of 20 mM $Mg^{2+}$ (lanes 1-3 and 7-9) or a mixture of 10 mM $Mg^{2+}$ and 5 mM $Mn^{2+}$ (lanes 4-6). The reaction mixtures that contained only normal NTPs (lanes 1, 4 and 7), both 2'-F-dCTP and 2'-F-dUTP (lanes 2, 5 and 8), or all four 2'-F-dNTPs (lanes 3, 6 and 9) are shown at the top of the gel. Products of transcription reactions were separated by native gel electrophoresis and then stained with ethidium bromide. The position of the migration of the DNA templates and the RNA products are marked on the left of the gel. The template used for the top gel is T22, which encodes a 37 nt transcript. The template used for the middle gel is T29, which encodes a 54 nt transcript. The template used for the bottom gel is T30, which encodes a 2,700 nt transcript. For each template, the sequence of the first nine nucleotides of the transcript is shown at the right of the gel, with the C and U residues in grey background.

The following three methods (I. wild-type Syn5 RNA polymerase with $Mg^{2+}$ alone; II. wild-type Syn5 RNA polymerase with a mixture of $Mg^{2+}$ and $Mn^{2+}$; and III. Syn5-Y564F RNA polymerase with $Mg^{2+}$ alone) were compared for their efficiency in transcribing different templates (FIG. 5). For the incorporation of 2'-F-dCMP and 2'-F-dUMP, wild-type Syn5 RNA polymerase with a mixture of $Mg^{2+}$ and $Mn^{2+}$ and Syn5-Y564F RNA polymerase with $Mg^{2+}$ alone are effective at producing a 37 nt RNA and a 54 nt RNA (FIG. 5 top and middle gels, lanes 5 and 8). However, wild-type Syn5 RNA polymerase with a mixture of $Mg^{2+}$ and $Mn^{2+}$ results in a superior yield (>0.8 µg/µl reaction). With $Mg^{2+}$, $Mn^{2+}$ and wild-type Syn5 RNA polymerase, all four rNMPs can be substituted with 2'-F-dNMPs at a yield of ~0.1 µg/µl reaction. The use of wild-type Syn5 RNA polymerase with just $Mg^{2+}$ ions is effective only when the small RNA product has no U and one C in the first 9 nucleotides of the transcript (FIG. 5 middle gel, lane 2); however, this standard reaction mixture does provide a simple and robust method of transcription of such small RNAs containing 2'-fluoro substitutions.

For the production of long 2'-F RNAs, Syn5-Y564F RNA polymerase is the most efficient enzyme on templates that contain an optimized initiation region (FIG. 4A, lane 10 vs. FIG. 3C, lane 8). Syn5-Y564F RNA polymerase was tested on a very difficult template that produces a transcript starting with GGG and contains two U's in the first nine nucleotides of the transcript (template T30). Although the yield on this template is low (FIG. 2B lane 13), a prolonged incubation to 8 hours significantly increases the yield (FIG. 5 bottom gel, lane 1), allowing comparison of the various methods to optimize the amount of product synthesized. Syn5-Y564F RNA polymerase was superior to wild-type Syn5 RNA polymerase for the incorporation of 2'-F-dCMP and 2'-F-dUMP (FIG. 5 bottom gel, lane 8 vs. lanes 5 and 2). However, for the incorporation of all four 2'-F-dNMPs into the transcript produced on this template, the only conditions that produced any full-length product were those using wild-type Syn5 RNA polymerase with a mixture of $Mg^{2+}$ and $Mn^{2+}$ ions. Under these conditions, the efficiency was low (FIG. 5 bottom gel, lane 6).

Figure 6:
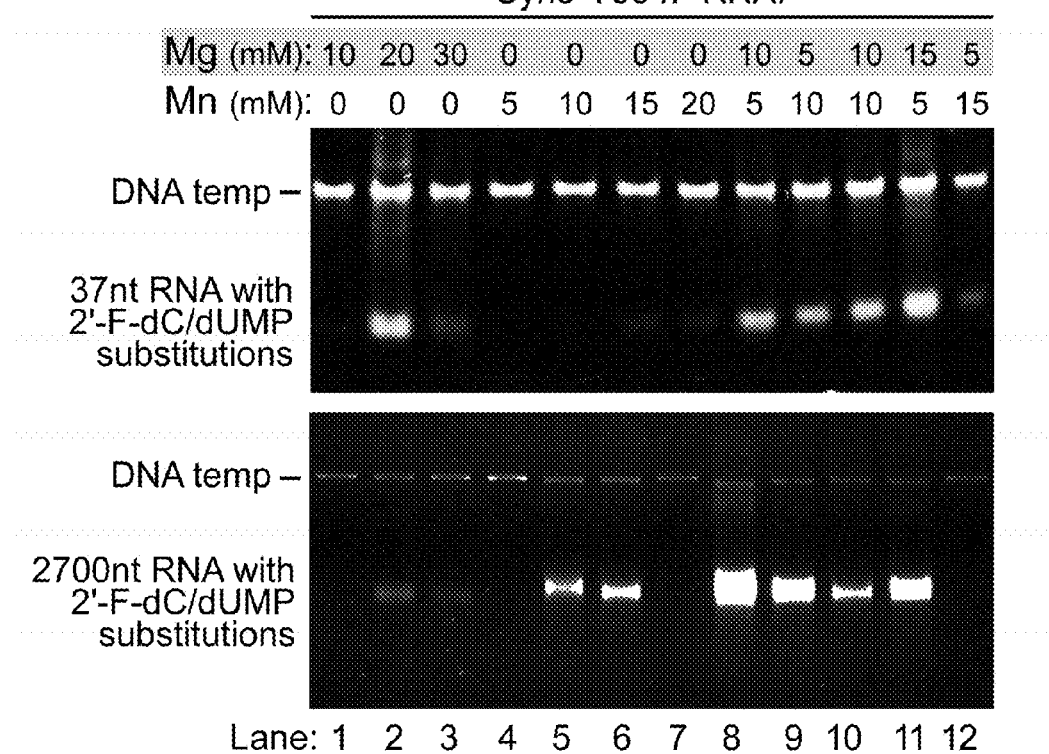
FIG. 6 is directed to the effect of $Mn^{2+}$ ions on 2'-F-dNMP incorporation by SynS-Y564F RNA polymerase. Transcription reactions were carried out by SynS-Y564F RNA polymerase. The metal ion present in each reaction and its concentration are shown at the top of the gel. All the reaction mixtures contained ATP, GTP, 2'-F-dCTP and 2'-F-dUTP. Products of transcription reactions were separated by native gel electrophoresis and then stained with ethidium bromide. The position of the migration of the DNA templates and the transcripts are marked. The template used for the top gel is T22, which encodes a 37 nt transcript. The template used for the bottom gel is T30, which encodes a 2,700 nt transcript.

The effect of $Mn^{2+}$ on the 2'-F RNA synthesis catalyzed by Syn5-Y564F RNA polymerase was tested and the addition of $Mn^{2+}$ did not improve the yield of a small 2'-F RNA (37 nt) with 2'-F-dCMP and 2'-F-dUMP substitutions as it does for wild-type enzyme (FIG. 3A) at all conditions tested (FIG. 6 upper gel, lanes 4-12 vs. 2). However, in many reactions containing $Mn^{2+}$, the yield of a long 2'-F RNA (2,700 nt) with 2'-F-dCMP and 2'-F-dUMP substitutions is significantly improved compared to that with $Mg^{2+}$ only (FIG. 6 bottom gel, lanes 5, 6, 8-11 vs. 2). The highest yield was observed with a combination of 10 mM $Mg^{2+}$ and 5 mM $Mn^{2+}$ (FIG. 6 bottom gel, lane 8). However, the yield of 2'-F DNA with full 2'-F-dNMP substitutions by Syn5-Y564F RNA polymerase with any combination of $Mg^{2+}$ and $Mn^{2+}$ tested is too low to be detected (FIG. 10).

Figure 7:
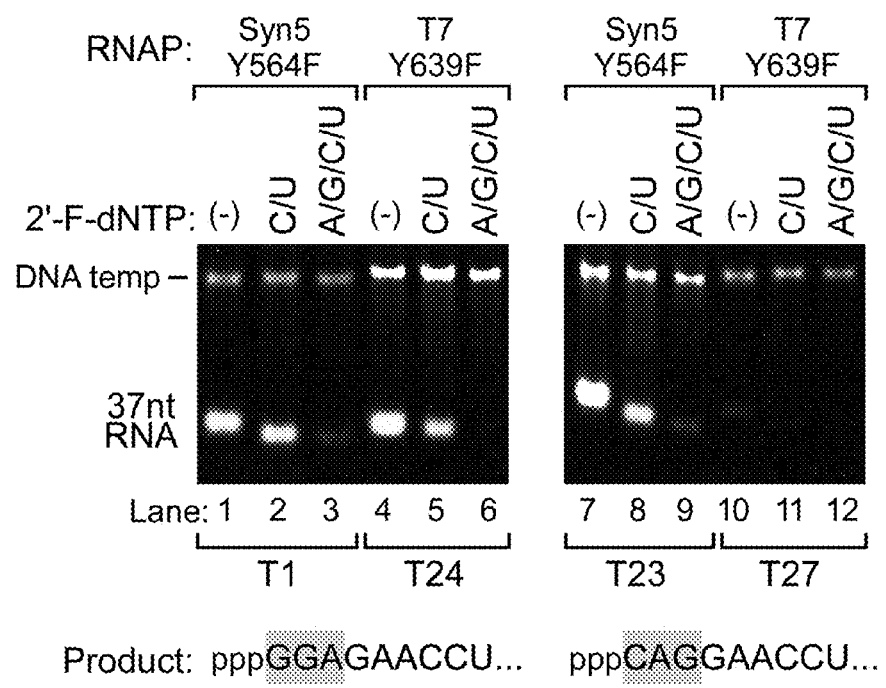
FIG. 7 is directed to synthesis of 2'-F RNAs by SynS-Y564F and T7-Y639F RNA polymerases. Transcription reactions were carried out using either SynS-Y564F RNA polymerase (lanes 1-3 and 7-9) or T7-Y639F RNA polymerase (lanes 4-6 and 10-12). The reaction mixtures that contained only normal NTPs (lanes 1, 4, 7 and 10), both 2'-F-dCTP and 2'-F-dUTP (lanes 2, 5, 8 and 11), or all four 2'-F-dNTPs (lanes 3, 6, 9 and 12) are shown at the top of the gel. Products of transcription reactions were separated by native gel electrophoresis and then stained with ethidium bromide. The position of the migration of the DNA templates and the RNA products are marked on the left of the gel. The template used for the experiments shown in the left gel is T1 (for SynS-Y564F RNA polymerase) and T24 (for T7-Y639F RNA polymerase), which encode 37 nt transcripts of the same sequence starting with GGA. The template used for the right gel is T23 (for SynS-Y564F RNA polymerase) and T27 (for T7-Y639F RNA polymerase), which encode 37 nt transcripts of the same sequence starting with CAG. For each template, the sequence of the first nine nucleotides of the transcript is shown at the bottom of the gel, with the first three residues in a grey background.

Syn5-Y564F RNA polymerase was compared to T7-Y639F RNA polymerase for synthesis of 2'-F RNA (2'-F DNA), using various initial sequences in the template (FIG. 7). When the transcripts start with GGA, both enzymes efficiently produce 2'-F RNA with 2'-F-dCMP and 2'-F-dUMP substitutions (FIG. 7, lanes 2 and 5). Although the yield of natural RNA is similar for both enzymes (FIG. 7, lane 1 vs. 4), the yield of 2'-F RNA with 2'-F-dCMP and 2'-F-dUMP substitutions synthesized by T7-Y639F RNA polymerase is lower than that synthesized by Syn5-Y564F RNA polymerase (FIG. 7, lane 2 vs. 5). 2'-F DNA with full substitutions synthesized by Syn5-Y564F RNA polymerase (FIG. 7, lane 3) is not observed with T7-Y639F RNA polymerase (FIG. 7, lane 6), indicating that T7-Y639F RNA polymerase has stronger discrimination against 2'-F-dNTPs, especially 2'-F-dGTP and/or 2'-F-dATP than does Syn5-Y564F RNA polymerase. When the transcripts start with CAG, Syn5-Y564F RNA polymerase showed a similar yield with that for transcripts starting with GGA (FIG. 7, lanes 7-9). In the latter case the products synthesized by T7-Y639F RNA polymerase, even natural RNA, are barely detectable. Syn5-Y564F RNA polymerase is advantageous to synthesize 2'-F RNA (2'-F DNA) that is heavily modified and to synthesize transcripts containing initial sequences that are not synthesized effectively by T7 RNA polymerase. Accordingly, methods are provided for transcription using Syn5 RNAP or a mutant thereof under conditions described herein where the transcript includes one or more of 2'-F-dCMP, 2'-F-dUMP, 2'-F-dAMP and 2'-F-dGMP. According to one aspect, methods are provided for transcription using Syn5 RNAP or a mutant thereof under conditions described herein where each nucleotide of the transcript is 2'-F-dNMP, where 2'-F-dNMP is one of 2'-F-dCMP, 2'-F-dUMP, 2'-F-dAMP and 2'-F-dGMP.

Example IX

Table 1 lists transcription product yields of reactions as shown in the Figures. Transcription yield was calculated based on comparison of the intensity of the product band to that of the DNA template band. [a]n.d., not detected. [b]Yield quantified by measurement of the purified transcript as described herein.

| Reaction (10 μl) corresponding to | | Product yield (μg) |
|---|---|---|
| FIG. Lane | 1A | |
| | 1 | 4.5 |
| | 2-3 | n.d.[a] |
| | 4 | 0.1 |
| | 5 | 0.2 |
| | 6 | n.d. |
| | 7 | 2.5 |
| | 8, 9 | n.d. |
| | 10 | 1.1 |
| | 11 | 0.4 |
| | 12 | 1.0 |
| | 13 | n.d. |
| | 14 | 2.2 |
| | 15 | n.d. |
| | 16 | 0.8 |
| | 17 | 1.8 |
| | 18 | 0.4 |
| | 19 | 0.2 |
| | 20 | n.d. |
| FIG. Lane | 1B | |
| | 1 | 46 |
| | 2 | 38 |
| | 3 | 32 |
| | 4 | 23 |
| | 5 | 45 |
| | 6 | n.d. |
| | 7 | 23 |
| FIG. Lane | 2A | |
| | 1 | 39 |
| | 2 | 2.1 |
| | 3 | 22 |
| | 4 | 14 |
| | 5 | 48 |
| | 6 | n.d. |
| | 7 | n.d. |
| | 8 | 48 |
| | 9 | n.d. |
| | 10 | 6.2 |
| | 11 | 0.1 |
| | 12 | 6.8 |
| | 13 | 30 |
| | 14 | 36 |
| | 15 | 24 |
| FIG. Lane | 2B | |
| | 1 | 50 |
| | 2 | 17 |
| | 3 | 1.7 |
| | 4 | 1.8 |
| | 5 | 6.2 |
| | 6 | 12 |
| | 7 | 7.6 |
| | 8 | 8.0 |
| | 9 | 14 |
| | 10 | 12 |
| | 11 | 1.1 |
| | 12 | 13 |
| | 13 | 0.6 |
| | 14 | 70[b] |
| FIG. Lane | 2C | |
| | 1 | 1.5 |
| | 2 | 5.5 |
| | 3 | 11 |
| | 4 | 4.0 |
| | 5 | 9.3 |
| | 6 | 13 |
| | 7 | 1.3 |
| | 8 | 2.5 |
| | 9 | 3.7 |
| FIG. Lane | 2D | |
| | 1 | 42 |
| | 2 | 15 |
| | 3 | 22 |
| | 4 | 20 |
| FIG. Lane | 2E | |
| | 1 | 14 |
| | 2 | 1.1 |
| | 3 | 45 |
| | 4 | 23 |
| FIG. Lane | 3A | |
| | 1 | — |
| | 2 | 6.1 |
| | 3-5 | n.d. |
| | 6 | 0.3 |
| | 7 | 0.1 |
| | 8 | 0.7 |

-continued

| Reaction (10 µl) corresponding to | | Product yield (µg) |
|---|---|---|
| | 9 | 0.1 |
| | 10 | 1.4 |
| | 11 | 0.4 |
| | 12 | 1.7 |
| | 13 | 0.3 |
| FIG. Lane | 3B | |
| | 1 | 5.7 |
| | 2 | n.d. |
| | 3 | 1.6 |
| | 4 | 0.3 |
| | 5 | 3.9 |
| | 6 | 0.8 |
| | 7 | 0.5 |
| | 8 | 2.7 |
| | 9 | 0.3 |
| | 10 | 0.5 |
| | 11 | 2.1 |
| | 12 | 0.1 |
| | 13 | 0.1 |
| FIG. Lane | 3C | |
| | 1 | 17 |
| | 2, 3 | n.d. |
| | 4 | 12 |
| | 5 | 6.1 |
| | 6 | 1.3 |
| | 7 | 70 |
| | 8 | n.d. |
| FIG. Lane | 4A | |
| | 1 | 15 |
| | 2 | n.d. |
| | 3 | 11 |
| | 4 | 4.0 |
| | 5 | 14 |
| | 6 | n.d. |
| | 7 | 70 |
| | 8 | n.d. |
| | 9 | 28 |
| | 10 | 10 [b] |
| | 11 | 62 |
| | 12 | n.d. |
| FIG. Lane | 4B | |
| | 1 | 22 |
| | 2, 3 | n.d. |
| | 4 | 13 |
| | 5 | 12 |
| | 6 | 4.7 |
| | 7 | n.d. |
| | 8 | 2.4 |
| | 9 | 0.1 |
| | 10 | 0.4 |
| | 11 | 0.8 |
| | 12 | 0.9 |
| | 13 | 2.7 |
| | 14 | 1.4 |
| FIG. Lane | 5 top gel | |
| | 1 | 16 |
| | 2, 3 | n.d. |
| | 4 | 14 |
| | 5 | 8.0 |
| | 6 | 1.5 |
| | 7 | 11 |
| | 8 | 2.8 |
| | 9 | 0.5 |
| FIG. Lane | 5 middle gel | |
| | 1 | 18 |
| | 2 | 8.8 |
| | 3 | n.d. |
| | 4 | 17 [b] |
| | 5 | 10 [b] |
| | 6 | 1.2 [b] |
| | 7 | 16 |
| | 8 | 8 |
| | 9 | 0.2 |
| FIG. Lane | 5 bottom gel | |
| | 1 | 10 |
| | 2, 3 | n.d. |
| | 4 | 2.5 |
| | 5 | 0.2 |
| | 6 | n.d. |
| | 7 | 2.0 |
| | 8 | 0.9 |
| | 9 | n.d. |
| FIG. Lane | 6 top gel | |
| | 1 | n.d. |
| | 2 | 3.5 |
| | 3 | 0.4 |
| | 4, 5 | n.d. |
| | 6 | 0.1 |
| | 7 | 0.2 |
| | 8 | 1.0 |
| | 9 | 0.7 |
| | 10 | 1.2 |
| | 11 | 3.4 |
| | 12 | 0.4 |
| FIG. Lane | 6 bottom gel | |
| | 1 | n.d. |
| | 2 | 0.8 |
| | 3 | 0.2 |
| | 4 | n.d. |
| | 5 | 2.5 |
| | 6 | 3.1 |
| | 7 | n.d. |
| | 8 | 20 [b] |
| | 9 | 11 |
| | 10 | 2.6 |
| | 11 | 9.8 |
| | 12 | n.d. |
| FIG. Lane | 7 | |
| | 1 | 6.1 |
| | 2 | 3.9 |
| | 3 | 0.6 |
| | 4 | 7.5 |
| | 5 | 1.9 |
| | 6 | n.d. |
| | 7 | 6.6 |
| | 8 | 3.2 |
| | 9 | 0.7 |
| | 10 | 0.7 |
| | 11, 12 | n.d. |

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A method of performing in vitro transcription comprising the steps of:

combining a double stranded nucleic acid including a template strand and a coding strand, a cyanophage Syn5 RNA polymerase (RNAP) or cyanophage Syn5 RNAP Y564F mutant, one or more nucleotides, one or more modified nucleotides and one or more of 3'-fluoro-dCTP, or 2'-fluoro-dUTP, and producing a transcript, wherein the double stranded nucleic acid includes a cyanophage Syn5 RNAP promoter sequence comprising SEQ ID NO: 1, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence, wherein nt is dCMP, dGMP, dAMP or dTMP and wherein nucleotides $nt_1$-$nt_2$-$nt_3$-$nt_4$-$nt_5$-$nt_6$-$nt_7$-$nt_8$-$nt_9$ include no more than 2 dTMPs or no more than 2 dCMPs with the remaining nucleotides being one or more of dGMP or dAMP with the proviso that nucleotides $nt_1$-$nt_2$-$nt_3$-$nt_4$-$nt_5$-$nt_6$-$nt_7$-$nt_8$-$nt_9$ cannot include 2 dTMPs and 2 dCMPs.

2. The method of claim 1, wherein the combining includes the presence of $Mn^{2+}$ in a concentration range of 5 mM to 20 mM or $Mg^{2+}$ in a concentration range of 10 mM to 20 mM.

3. The method of claim 1, wherein the conditions suitable for producing a transcript include the presence of $Mg^{2+}$ in a concentration range of 10 mM to 20 mM and $Mn^{2+}$ in a concentration range of 5 mM to 20 mM.

4. The method of claim 1, wherein the conditions suitable for producing a transcript include the presence of $Mg^{2+}$ in a concentration of 10 mM and $Mn^{2+}$ in a concentration of 5 mM.

5. The method of claim 1 wherein the transcript includes one or more of 2'-fluoro-dCMP or 2'-fluoro-dUMP.

6. The method of claim 1 wherein nucleotides $nt_1$-$nt_2$-$nt_3$-$nt_4$-$nt_5$-$nt_6$-$nt_7$-$nt_8$-$nt_9$ include no more than 1 dCMP or no more than 1 dTMP with the remaining nucleotides being one or more of dGMP or dAMP.

7. The method of claim 1 wherein nucleotides $nt_1$-$nt_2$-$nt_3$-$nt_4$-$nt_5$-$nt_6$-$nt_7$-$nt_8$-$nt_9$ include no dCMP and no more than 2 dTMPs with the remaining nucleotides being one or more of dGMP or dAMP.

8. The method of claim 1 wherein nucleotides $nt_1$-$nt_2$-$nt_3$-$nt_4$-$nt_5$-$nt_6$-$nt_7$-$nt_8$-$nt_9$ include no dTMP and no more than 2 dCMPs with the remaining nucleotides being one or more of dGMP or dAMP.

9. The method of claim 1 wherein nucleotides $nt_1$-$nt_2$-$nt_3$-$nt_4$-$nt_5$-$nt_6$-$nt_7$-$nt_8$-$nt_9$ include no dTMP and no more than 3 dCMPs.

10. The method of claim 1 wherein nucleotides $nt_1$-$nt_2$-$nt_3$-$nt_4$-$nt_5$-$nt_6$-$nt_7$-$nt_8$-$nt_9$ include no dCMP and no dTMP and with the remaining nucleotides being one or more of dGMP or dAMP.

11. The method of claim 1 wherein nucleotides $nt_1$-$nt_2$-$nt_3$ include no dTMP.

12. The method of claim 1 wherein nucleotides $nt_1$-$nt_2$-$nt_3$ are dGMP-dGMP-dAMP, dGMP-dAMP-dAMP, dAMP-dGMP-dAMP, dGMP-dCMP-dAMP, or dCMP-dAMP-dGMP.

13. The method of claim 1 wherein nucleotides $nt_1$-$nt_2$-$nt_3$-$nt_4$-$nt_5$-$nt_6$-$nt_7$-$nt_8$-$nt_9$ include no dAMP in series of 4 or more.

14. The method of claim 1 wherein nucleotides $nt_1$-$nt_2$-$nt_3$-$nt_4$-$nt_5$-$nt_6$-$nt_7$-$nt_8$-$nt_9$ or portions thereof beginning at $nt_1$ are dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dAMP-dGMP, dGMP-dCMP-dAMP-dGMP-dAMP-dAMP-dGMP-dAMP or dGMP-dCMP-dAMP-dGMP-dAMP-dAMP-dGMP-dAMP.

15. The method of claim 1, wherein the transcript is mRNA, tRNA, rRNA, miRNA, siRNA, snRNA, snoRNA, a ribozyme, an aptamer or an RNA fragment.

16. The method of claim 1, wherein the combining includes the presence of salt at a concentration of at least about 100 mM.

17. The method of claim 1, wherein the combining includes the presence of a salt at a concentration of at least about 160 mM.

18. The method of claim 1, wherein the combining includes the presence of a salt at a concentration of at least about 200 mM.

19. The method of claim 1, wherein the combining includes the presence of a salt at a concentration of about 250 mM.

20. The method of claim 1, wherein the combining includes the presence of KCl or NaCl.

21. The method of claim 1, wherein the combining includes a temperature within the range of 4° C. and 37° C.

22. The method of claim 1, wherein the combining includes a temperature within the range of 10° C. and 25° C.

23. The method of claim 1, wherein the combining includes a temperature within the range of 14° C. and 22° C.

24. The method of claim 1, wherein the combining includes a temperature of 16° C.

25. The method of claim 1, wherein the one or more modified nucleotides is 2'-F-dATP, 2'-F-dGTP, 2'-$NH_2$-dATP, 2'-$NH_2$-dGTP, 2'-$NH_2$-dCTP, 2'-$NH_2$-dUTP, 2'-OMe-dATP, 2'-OMe-dGTP, 2'-OMe-dCTP, or 2'-OMe-dUTP.

26. The method of claim 1, wherein the cyanophage Syn5 RNAP or the cyanophage Syn5 RNAP Y564F mutant includes a heterologous polypeptide sequence.

27. The method of claim 1, wherein the cyanophage Syn5 RNAP or the cyanophage Syn5 RNAP Y564F mutant includes a protein tag selected from the group consisting of one or any combination of Avi tag, calmodulin tag, FLAG tag, HA tag, His tag, Myc tag, S tag, SBP tag, Softag 1, Softag 3, V5 tag, Xpress tag, Isopeptag, SpyTag, biotin carboxyl carrier protein tag, glutathione-s-tranferase tag, green fluorescent protein tag, maltose binding protein tag, Nus tag, streptavidin tag, streptactin tag, and thioredoxin tag.

28. The method of claim 1, wherein the cyanophage Syn5 RNAP or the Syn5 RNAP Y564F mutant includes a removable protein tag.

29. The method of claim 1, wherein the transcripts are greater than about 10,000 nucleotides in length.

30. The method of claim 1, wherein the transcripts are greater than about 20,000 nucleotides in length.

31. The method of claim 1, wherein the transcripts are greater than about 30,000 nucleotides in length.

32. The method of claim 1, wherein greater than about 90% of the transcripts contain homogeneous 3' ends.

33. The method of claim 1, wherein greater than about 95% of the transcripts contain homogeneous 3' ends.

34. The method of claim 1, wherein greater than about 99% of the transcripts contain homogeneous 3' ends.

35. The method of claim 1, wherein greater than about 90% of the transcripts contain precisely terminated 3' ends.

36. The method of claim 1, wherein greater than about 95% of the transcripts contain precisely terminated 3' ends.

37. The method of claim 1, wherein greater than about 99% of the transcripts contain precisely terminated 3' ends.

38. The method of claim 1, wherein greater than about 90% of the transcripts lack a nucleotide overhang at the 3' ends.

39. The method of claim 1, wherein greater than about 95% of the transcripts lack a nucleotide overhang at the 3' ends.

40. The method of claim 1, wherein greater than about 99% of the transcripts lack a nucleotide overhang at the 3' ends.

41. The method of claim 1 wherein the cyanophage Syn5 RNA polymerase is an isolated cyanophage Syn5 RNA polymerase.

42. The method of claim 1 wherein the cyanophage Syn5 RNA polymerase is a purified cyanophage Syn5 RNA polymerase.

43. The method of claim 1 wherein the cyanophage Syn5 RNA polymerase is a synthesized cyanophage Syn5 RNA polymerase.

44. The method of claim 1, wherein less than 20% of the transcripts contain a nucleotide overhang at their 3' ends.

45. The method of claim 1, wherein less than 10% of the transcripts contain a nucleotide overhang at their 3' ends.

46. The method of claim 1, wherein less than 5% of the transcripts contain a nucleotide overhang at their 3' ends.

47. The method of claim 1, wherein less than 1% of the transcripts contain a nucleotide overhang at their 3' ends.

48. The method of claim 1 wherein the nucleic acid template sequence is a DNA template sequence and the transcript includes fewer than three 2'-modified nucleotides within the first 12 nucleotides of the transcript and wherein the fewer than three 2'-modified nucleotides within the first 12 nucleotides are non-consecutive.

49. The method of claim 1 wherein the nucleic acid template sequence includes a sequence which when transcribed by the cyanophage Syn5 RNAP produces a transcript including fewer than three 2'-modified nucleotides within the first 12 nucleotides of the transcript.

50. A method of performing in vitro transcription comprising the steps of:
   combining a double stranded nucleic acid including a template strand and a coding strand, a cyanophage Syn5 RNAP or cyanophage Syn5 RNAP mutant Y564F, one or more nucleotides, one or more modified nucleotides and one or more of 2'-fluoro-dCTP, or 2'-fluoro-dUTP, and
   producing a transcript,
   wherein the double stranded nucleic acid includes a cyanophage Syn5 RNAP promoter sequence comprising SEQ ID NO: 1,
   wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence,
   wherein the first 9 nucleotides are altered to include beginning at $nt_1$ one of dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dAMP-dGMP, dGMP-dCMP-dAMP-dGMP-dAMP-dAMP-dGMP-dAMP or dGMP-dCMP-dAMP-dGMP-dAMP-dAMP-dGMP-dAMP-dAMP.

51. A method of performing in vitro transcription comprising the steps of:
   combining a double stranded nucleic acid including a template strand and a coding strand, a cyanophage Syn5 RNAP or cyanophage Syn5 RNAP mutant Y564F, one or more nucleotides, one or more modified nucleotides and one or more of 2'-fluoro-dCTP, or 2'-fluoro-dUTP,
   wherein the double stranded nucleic acid includes a cyanophage Syn5 RNAP promoter sequence comprising SEQ ID NO: 1,
   wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence,
   wherein one or more of dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dAMP-dGMP, dGMP-dCMP-dAMP-dGMP-dAMP-dAMP-dGMP-dAMP or dGMP-dCMP-dAMP-dGMP-dAMP-dAMP-dGMP-dAMP-dAMP is added to the coding strand after the promoter sequence and before the initiation sequence to create an altered initiation sequence of 12 nucleotides after the promoter sequence with complementary nucleotides added to the template strand, and
   producing a transcript.

52. A method of performing in vitro transcription comprising the steps of:
   combining a double stranded nucleic acid including a template strand and a coding strand, a cyanophage Syn5 RNAP or cyanophage Syn5 RNAP mutant Y564F, one or more nucleotides, one or more modified nucleotides and one or more of 2'-fluoro-dCTP, or 2'-fluoro-dUTP,
   wherein the double stranded nucleic acid includes a cyanophage Syn5 RNAP promoter sequence comprising SEQ ID NO: 1,
   wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence,
   wherein one or more of sequence dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMP-dGMP-dAMP-dAMP-dGMP, dGMP-dCMP-dAMP-dGMP-dAMP-dAMP-dGMP-dAMP or dGMP-dCMP-dAMP-dGMP-dAMP-dAMP-dGMP-dAMP-dAMP
   coupled to a removable RNA element is added to the coding strand after the promoter sequence and before the initiation sequence to create an altered initiation sequence of 12 nucleotides after the promoter sequence with complementary nucleotides added to the template strand, and
   producing a transcript.

53. The method of claim 52 wherein the removable RNA element is a ribozyme.

54. The method of claim 52 wherein the ribozyme and the added sequence is removed from the transcript.

55. A method of performing in vitro transcription comprising the steps of:
   combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U,
   wherein the double stranded nucleic acid includes a cyanophage Syn5 RNAP promoter sequence comprising SEQ ID NO: 1,
   wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same rXMP where X is A, G, C, T or U within the first 9 nt,
   wherein one or more of sequence dGMP, dGMP-dCMP, dGMP-dCMP-dAMP, dGMP-dCMP-dAMP-dGMP, dGMP-dCMP-dAMP-dGMP-dAMP, dGMP-dCMP-dAMP-dGMP-dAMP-dAMP, dGMP-dCMP-dAMPdGMP-dAMP-dAMP-dGMP, dGMP-dCMP-dAMP-dGMP-dAMP-dAMP-dGMP-dAMP or dGMP-dCMP-dAMP-dGMP-dAMP-dGMP-dAMP-dAMP is added to the coding strand after the promoter sequence and before the initiation sequence to create an altered initiation sequence of 12 nucleotides after the promoter sequence with complementary nucleotides added to the template strand, and producing a transcript.

56. A method of performing in vitro transcription comprising the steps of:

combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U, wherein the double stranded nucleic acid includes a cyanophage Syn5 RNAP promoter sequence comprising SEQ ID NO: 1, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same dXMP where X is A, G, C, or T or U within the first 9 nt, wherein the coding strand is modified to include 2 or fewer of the dXMP, where X is A, G, C, or T, within the first 9 nucleotides to improve the incorporation of 2'-fluoro-dXMP, where X is A, G, C or U, respectively, into the entire transcript, and producing a transcript.

57. The method of claim 56 wherein the removable RNA element is a ribozyme.

58. The method of claim 56 wherein the ribozyme and the added sequence is removed from the transcript.

59. A method of performing in vitro transcription comprising the steps of:

combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U, wherein the double stranded nucleic acid includes a cyanophage Syn5 RNAP promoter sequence comprising SEQ ID NO: 1, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same rXMP where X is A, G, C, T or U within the first 9 nt, altering the promoter sequence to include 2 or fewer of the same dXMP where X is A, G, C, T or U within the first 9 nt.

60. A method of performing in vitro transcription comprising the steps of:

combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U, wherein the double stranded nucleic acid includes a cyanophage Syn5 RNAP promoter sequence comprising SEQ ID NO: 1, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same dXMP where X is A, G, C, or T within the first 9 nt, wherein one or more dNMP is added to the coding strand after the promoter sequence with complementary nucleotides added to the template strand so that the coding strand is modified to include 2 or fewer of the dXMP (where X is A, G, C, or T) within the first 9 nt to facilitate the incorporation of 2'-fluoro-dXMP (where X is A, G, C, or U, respectively) into the entire transcript, and producing a transcript.

61. A method of performing in vitro transcription comprising the steps of:

combining a double stranded nucleic acid including a template strand and a coding strand, a cyanophage Syn5 RNAP or cyanophage Syn5 RNAP mutant Y564F, one or more of 2'-fluoro-dNTP, where N is A, G, C, T or U, wherein the double stranded nucleic acid includes a cyanophage Syn5 RNAP promoter sequence comprising SEQ ID NO: 1, wherein the coding strand includes an initiation sequence of 12 nucleotides $nt_1$-$nt_2$-$nt_3$-$nt_4$-$nt_5$-$nt_6$-$nt_7$-$nt_8$-$nt_9$-$nt_{10}$-$nt_{11}$-$nt_{12}$ after the promoter sequence including 3 or more of the same dXMP where X is A, G, C, or T within the first 9 nt, wherein one or more dNMP coupled to a removable RNA element is added to the coding strand after the promoter sequence with complementary nucleotides added to the template strand so that the coding strand is modified to include 2 or fewer of the dXMP (where X is A, G, C, or T) within the first 9 nt to facilitate the incorporation of 2'-fluoro-dXMP (where X is A, G, C, or U, respectively) into the entire transcript, and producing a transcript.

* * * * *

SEQUENCE LISTING

<160> NUMBER OF SEQ ID NOS: 76

<210> SEQ ID NO 1

```
<211> LENGTH: 15
<212> TYPE: DNA
<213> ORGANISM: ARTIFICIAL
<220> FEATURE:
<223> OTHER INFORMATION: Syn5 RNAP promoter

<400> SEQUENCE: 1
attgggcacc cgtaa                                                    15

<210> SEQ ID NO 2
<211> LENGTH: 15
<212> TYPE: PRT
<213> ORGANISM: ARTIFICIAL
<220> FEATURE:
<223> OTHER INFORMATION: Avi tag

<400> SEQUENCE: 2

Gly Leu Asn Asp Ile Phe Glu Ala Gln Lys Ile Glu Trp His Glu
1               5                   10                  15

<210> SEQ ID NO 3
<211> LENGTH: 26
<212> TYPE: PRT
<213> ORGANISM: ARTIFICIAL
<220> FEATURE:
<223> OTHER INFORMATION: calmodulin tag

<400> SEQUENCE: 3

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 4
<211> LENGTH: 8
<212> TYPE: PRT
<213> ORGANISM: ARTIFICIAL
<220> FEATURE:
<223> OTHER INFORMATION: FLAG tag

<400> SEQUENCE: 4

Asp Tyr Lys Asp Asp Asp Asp Lys
1               5

<210> SEQ ID NO 5
<211> LENGTH: 9
<212> TYPE: PRT
<213> ORGANISM: ARTIFICIAL
<220> FEATURE:
<223> OTHER INFORMATION: HA tag

<400> SEQUENCE: 5

Tyr Pro Tyr Asp Val Pro Asp Tyr Ala
1               5

<210> SEQ ID NO 6
<211> LENGTH: 6
<212> TYPE: PRT
<213> ORGANISM: ARTIFICIAL
<220> FEATURE:
<223> OTHER INFORMATION: His tag

<400> SEQUENCE: 6

His His His His His His
1               5
```

```
<210> SEQ ID NO 7
<211> LENGTH: 10
<212> TYPE: PRT
<213> ORGANISM: ARTIFICIAL
<220> FEATURE:
<223> OTHER INFORMATION: Myc tag

<400> SEQUENCE: 7

Glu Gln Lys Leu Ile Ser Glu Glu Asp Leu
1               5                   10

<210> SEQ ID NO 8
<211> LENGTH: 15
<212> TYPE: PRT
<213> ORGANISM: ARTIFICIAL
<220> FEATURE:
<223> OTHER INFORMATION: S tag

<400> SEQUENCE: 8

Lys Glu Thr Ala Ala Ala Lys Phe Glu Arg Gln His Met Asp Ser
1               5                   10                  15

<210> SEQ ID NO 9
<211> LENGTH: 38
<212> TYPE: PRT
<213> ORGANISM: ARTIFICIAL
<220> FEATURE:
<223> OTHER INFORMATION: SBD tag

<400> SEQUENCE: 9

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 10
<211> LENGTH: 13
<212> TYPE: PRT
<213> ORGANISM: ARTIFICIAL
<220> FEATURE:
<223> OTHER INFORMATION: Soft tag 1

<400> SEQUENCE: 10

Ser Leu Ala Glu Leu Leu Asn Ala Gly Leu Gly Gly Ser
1               5                   10

<210> SEQ ID NO 11
<211> LENGTH: 8
<212> TYPE: PRT
<213> ORGANISM: ARTIFICIAL
<220> FEATURE:
<223> OTHER INFORMATION: Soft tag 3

<400> SEQUENCE: 11

Thr Gln Asp Pro Ser Arg Val Gly
1               5

<210> SEQ ID NO 12
<211> LENGTH: 14
<212> TYPE: PRT
<213> ORGANISM: ARTIFICIAL
<220> FEATURE:
<223> OTHER INFORMATION: V5 tag

<400> SEQUENCE: 12
```

Gly Lys Pro Ile Pro Asn Pro Leu Leu Gly Leu Asp Ser Thr
1               5                   10

<210> SEQ ID NO 13
<211> LENGTH: 8
<212> TYPE: PRT
<213> ORGANISM: ARTIFICIAL
<220> FEATURE:
<223> OTHER INFORMATION: Xpress tag

<400> SEQUENCE: 13

Asp Leu Tyr Asp Asp Asp Asp Lys
1               5

<210> SEQ ID NO 14
<211> LENGTH: 16
<212> TYPE: PRT
<213> ORGANISM: ARTIFICIAL
<220> FEATURE:
<223> OTHER INFORMATION: Isopeptag

<400> SEQUENCE: 14

Thr Asp Lys Asp Met Thr Ile Thr Phe Thr Asn Lys Lys Asp Ala Glu
1               5                   10                  15

<210> SEQ ID NO 15
<211> LENGTH: 13
<212> TYPE: PRT
<213> ORGANISM: ARTIFICIAL
<220> FEATURE:
<223> OTHER INFORMATION: Spy Tag

<400> SEQUENCE: 15

Ala His Ile Val Met Val Asp Ala Tyr Lys Pro Thr Lys
1               5                   10

<210> SEQ ID NO 16
<211> LENGTH: 8
<212> TYPE: PRT
<213> ORGANISM: ARTIFICIAL
<220> FEATURE:
<223> OTHER INFORMATION: Step tag II

<400> SEQUENCE: 16

Trp Ser His Pro Gln Phe Glu Lys
1               5

<210> SEQ ID NO 17
<211> LENGTH: 55
<212> TYPE: DNA
<213> ORGANISM: ARTIFICIAL
<220> FEATURE:
<223> OTHER INFORMATION: DNA template

<400> SEQUENCE: 17
ggtattgggc acccgtaagg agaaccttaa ggtttaactt taagacccct aagtg        55

<210> SEQ ID NO 18
<211> LENGTH: 50
<212> TYPE: DNA
<213> ORGANISM: ARTIFICIAL
<220> FEATURE:
<223> OTHER INFORMATION: DNA template

<400> SEQUENCE: 18
gccattgggc acccgtaagg gagagagcat cgcttggtgc agatcgggac               50

```
<210> SEQ ID NO 19
<211> LENGTH: 89
<212> TYPE: DNA
<213> ORGANISM: ARTIFICIAL
<220> FEATURE:
<223> OTHER INFORMATION: DNA template

<400> SEQUENCE: 19
gccattgggc acccgtaaca gagaatagtt taaattagaa tcttagcttt gggtgctaat    60
ggtggagtta aagactttt ctctgacca                                       89

<210> SEQ ID NO 20
<211> LENGTH: 55
<212> TYPE: DNA
<213> ORGANISM: ARTIFICIAL
<220> FEATURE:
<223> OTHER INFORMATION: DNA template

<400> SEQUENCE: 20
ggtattgggc acccgtaagg agaagaagaa ggtttaactt taagacccct aagtg         55

<210> SEQ ID NO 21
<211> LENGTH: 55
<212> TYPE: DNA
<213> ORGANISM: ARTIFICIAL
<220> FEATURE:
<223> OTHER INFORMATION: DNA template

<400> SEQUENCE: 21
ggtattgggc acccgtaagg ggaagaagaa ggtttaactt taagacccct aagtg         55

<210> SEQ ID NO 22
<211> LENGTH: 55
<212> TYPE: DNA
<213> ORGANISM: ARTIFICIAL
<220> FEATURE:
<223> OTHER INFORMATION: DNA template

<400> SEQUENCE: 22
ggtattgggc acccgtaaga agaagaagaa ggtttaactt taagacccct aagtg         55

<210> SEQ ID NO 23
<211> LENGTH: 55
<212> TYPE: DNA
<213> ORGANISM: ARTIFICIAL
<220> FEATURE:
<223> OTHER INFORMATION: DNA template

<400> SEQUENCE: 23
ggtattgggc acccgtaaag agaagaagaa ggtttaactt taagacccct aagtg         55

<210> SEQ ID NO 24
<211> LENGTH: 55
<212> TYPE: DNA
<213> ORGANISM: ARTIFICIAL
<220> FEATURE:
<223> OTHER INFORMATION: DNA template

<400> SEQUENCE: 24
ggtattgggc acccgtaagc agaagaagaa ggtttaactt taagacccct aagtg         55

<210> SEQ ID NO 25
<211> LENGTH: 55
<212> TYPE: DNA
```

<213> ORGANISM: ARTIFICIAL
<220> FEATURE:
<223> OTHER INFORMATION: DNA template

<400> SEQUENCE: 25
ggtattgggc acccgtaagg aaaagaagaa ggtttaactt taagacccct aagtg     55

<210> SEQ ID NO 26
<211> LENGTH: 55
<212> TYPE: DNA
<213> ORGANISM: ARTIFICIAL
<220> FEATURE:
<223> OTHER INFORMATION: DNA template

<400> SEQUENCE: 26
ggtattgggc acccgtaagg atttgaagaa ggtttaactt taagacccct aagtg     55

<210> SEQ ID NO 27
<211> LENGTH: 55
<212> TYPE: DNA
<213> ORGANISM: ARTIFICIAL
<220> FEATURE:
<223> OTHER INFORMATION: DNA template

<400> SEQUENCE: 27
ggtattgggc acccgtaagg acccgaagaa ggtttaactt taagacccct aagtg     55

<210> SEQ ID NO 28
<211> LENGTH: 55
<212> TYPE: DNA
<213> ORGANISM: ARTIFICIAL
<220> FEATURE:
<223> OTHER INFORMATION: DNA template

<400> SEQUENCE: 28
ggtattgggc acccgtaagg agaaaaagaa ggtttaactt taagacccct aagtg     55

<210> SEQ ID NO 29
<211> LENGTH: 55
<212> TYPE: DNA
<213> ORGANISM: ARTIFICIAL
<220> FEATURE:
<223> OTHER INFORMATION: DNA template

<400> SEQUENCE: 29
ggtattgggc acccgtaagg agaagcggaa ggtttaactt taagacccct aagtg     55

<210> SEQ ID NO 30
<211> LENGTH: 55
<212> TYPE: DNA
<213> ORGANISM: ARTIFICIAL
<220> FEATURE:
<223> OTHER INFORMATION: DNA template

<400> SEQUENCE: 30
ggtattgggc acccgtaagg agaatttgaa ggtttaactt taagacccct aagtg     55

<210> SEQ ID NO 31
<211> LENGTH: 55
<212> TYPE: DNA
<213> ORGANISM: ARTIFICIAL
<220> FEATURE:
<223> OTHER INFORMATION: DNA template

<400> SEQUENCE: 31
ggtattgggc acccgtaagg agaacccgaa ggtttaactt taagacccct aagtg     55

<210> SEQ ID NO 32
<211> LENGTH: 55
<212> TYPE: DNA
<213> ORGANISM: ARTIFICIAL
<220> FEATURE:
<223> OTHER INFORMATION: DNA template

<400> SEQUENCE: 32
ggtattgggc acccgtaagg agaagaaaaa ggtttaactt taagacccctt aagtg    55

<210> SEQ ID NO 33
<211> LENGTH: 55
<212> TYPE: DNA
<213> ORGANISM: ARTIFICIAL
<220> FEATURE:
<223> OTHER INFORMATION: DNA template

<400> SEQUENCE: 33
ggtattgggc acccgtaagg agaagaattt ggtttaactt taagacccctt aagtg    55

<210> SEQ ID NO 34
<211> LENGTH: 55
<212> TYPE: DNA
<213> ORGANISM: ARTIFICIAL
<220> FEATURE:
<223> OTHER INFORMATION: DNA template

<400> SEQUENCE: 34
ggtattgggc acccgtaagg agaagaaccc ggtttaactt taagacccctt aagtg    55

<210> SEQ ID NO 35
<211> LENGTH: 55
<212> TYPE: DNA
<213> ORGANISM: ARTIFICIAL
<220> FEATURE:
<223> OTHER INFORMATION: DNA template

<400> SEQUENCE: 35
ggtattgggc acccgtaagg agtagaagaa ggtttaactt taagacccctt aagtg    55

<210> SEQ ID NO 36
<211> LENGTH: 55
<212> TYPE: DNA
<213> ORGANISM: ARTIFICIAL
<220> FEATURE:
<223> OTHER INFORMATION: DNA template

<400> SEQUENCE: 36
ggtattgggc acccgtaagg agtagtagaa ggtttaactt taagacccctt aagtg    55

<210> SEQ ID NO 37
<211> LENGTH: 55
<212> TYPE: DNA
<213> ORGANISM: ARTIFICIAL
<220> FEATURE:
<223> OTHER INFORMATION: DNA template

<400> SEQUENCE: 37
ggtattgggc acccgtaagg agttgaagaa ggtttaactt taagacccctt aagtg    55

<210> SEQ ID NO 38
<211> LENGTH: 55
<212> TYPE: DNA
<213> ORGANISM: ARTIFICIAL
<220> FEATURE:

<223> OTHER INFORMATION: DNA template

<400> SEQUENCE: 38
ggtattgggc acccgtaagc agaaccttaa ggtttaactt taagacccct aagtg    55

<210> SEQ ID NO 39
<211> LENGTH: 55
<212> TYPE: DNA
<213> ORGANISM: ARTIFICIAL
<220> FEATURE:
<223> OTHER INFORMATION: DNA template

<400> SEQUENCE: 39
ggtattgggc acccgtaaca ggaaccttaa ggtttaactt taagacccct aagtg    55

<210> SEQ ID NO 40
<211> LENGTH: 57
<212> TYPE: DNA
<213> ORGANISM: ARTIFICIAL
<220> FEATURE:
<223> OTHER INFORMATION: DNA template

<400> SEQUENCE: 40
ggttaatacg actcactata ggagaacctt aaggtttaac tttaagaccc ttaagtg    57

<210> SEQ ID NO 41
<211> LENGTH: 57
<212> TYPE: DNA
<213> ORGANISM: ARTIFICIAL
<220> FEATURE:
<223> OTHER INFORMATION: DNA template

<400> SEQUENCE: 41
ggttaatacg actcactata ggggaacctt aaggtttaac tttaagaccc ttaagtg    57

<210> SEQ ID NO 42
<211> LENGTH: 57
<212> TYPE: DNA
<213> ORGANISM: ARTIFICIAL
<220> FEATURE:
<223> OTHER INFORMATION: DNA template

<400> SEQUENCE: 42
ggttaatacg actcactata gcagaacctt aaggtttaac tttaagaccc ttaagtg    57

<210> SEQ ID NO 43
<211> LENGTH: 57
<212> TYPE: DNA
<213> ORGANISM: ARTIFICIAL
<220> FEATURE:
<223> OTHER INFORMATION: DNA template

<400> SEQUENCE: 43
ggttaatacg actcactata caggaacctt aaggtttaac tttaagaccc ttaagtg    57

<210> SEQ ID NO 44
<211> LENGTH: 57
<212> TYPE: DNA
<213> ORGANISM: ARTIFICIAL
<220> FEATURE:
<223> OTHER INFORMATION: DNA template

<400> SEQUENCE: 44
ggttaatacg actcactata ggagaagaag aaggtttaac tttaagaccc ttaagtg    57

```
<210> SEQ ID NO 45
<211> LENGTH: 72
<212> TYPE: DNA
<213> ORGANISM: ARTIFICIAL
<220> FEATURE:
<223> OTHER INFORMATION: DNA template

<400> SEQUENCE: 45
tccattgggc acccgtaagc agggaggacg atgcgggcct tcgtttgttt cgtccacaga    60
cgactcgccc ga                                                       72

<210> SEQ ID NO 46
<211> LENGTH: 55
<212> TYPE: DNA
<213> ORGANISM: ARTIFICIAL
<220> FEATURE:
<223> OTHER INFORMATION: DNA RNA template

<400> SEQUENCE: 46
ggtattgggc acccgtaaug agaaccttaa ggtttaactt taagaccctt aagtg         55

<210> SEQ ID NO 47
<211> LENGTH: 66
<212> TYPE: DNA
<213> ORGANISM: ARTIFICIAL
<220> FEATURE:
<223> OTHER INFORMATION: DNA template

<400> SEQUENCE: 47
attgggcacc cgtaagggag gacgatgcgg gccttcgttt gtttcgtcca cagacgactc    60
gcccga                                                              66

<210> SEQ ID NO 48
<211> LENGTH: 18
<212> TYPE: DNA
<213> ORGANISM: ARTIFICIAL
<220> FEATURE:
<223> OTHER INFORMATION: Plasmid pUC19 with a single Syn5 promoter and 3
      guanosine residues

<400> SEQUENCE: 48
attgggcacc cgtaaggg                                                 18

<210> SEQ ID NO 49

<400> SEQUENCE: 49

000

<210> SEQ ID NO 50

<400> SEQUENCE: 50

000

<210> SEQ ID NO 51
<211> LENGTH: 12
<212> TYPE: DNA
<213> ORGANISM: ARTIFICIAL
<220> FEATURE:
<223> OTHER INFORMATION: Syn5 RNA polymerase on template  T1

<400> SEQUENCE: 51
ggagaaccuu aa                                                       12
```

-continued

```
<210> SEQ ID NO 52
<211> LENGTH: 12
<212> TYPE: DNA
<213> ORGANISM: ARTIFICIAL
<220> FEATURE:
<223> OTHER INFORMATION: Syn5 RNA polymerase on template T2

<400> SEQUENCE: 52
gggagagagc au                                                             12

<210> SEQ ID NO 53
<211> LENGTH: 12
<212> TYPE: DNA
<213> ORGANISM: ARTIFICIAL
<220> FEATURE:
<223> OTHER INFORMATION: Syn5 RNA polymerase on template T3

<400> SEQUENCE: 53
cagagaauag uu                                                             12

<210> SEQ ID NO 54
<211> LENGTH: 12
<212> TYPE: DNA
<213> ORGANISM: ARTIFICIAL
<220> FEATURE:
<223> OTHER INFORMATION: Syn5 RNA polymerase on template T4

<400> SEQUENCE: 54
ggagaagaag aa                                                             12

<210> SEQ ID NO 55
<211> LENGTH: 12
<212> TYPE: DNA
<213> ORGANISM: ARTIFICIAL
<220> FEATURE:
<223> OTHER INFORMATION: template T4

<400> SEQUENCE: 55
ggagaagaag aa                                                             12

<210> SEQ ID NO 56
<211> LENGTH: 10
<212> TYPE: DNA
<213> ORGANISM: ARTIFICIAL
<220> FEATURE:
<223> OTHER INFORMATION: template T19

<400> SEQUENCE: 56
ggaguagaag                                                                10

<210> SEQ ID NO 57
<211> LENGTH: 10
<212> TYPE: DNA
<213> ORGANISM: ARTIFICIAL
<220> FEATURE:
<223> OTHER INFORMATION: template T20

<400> SEQUENCE: 57
ggaguaguag                                                                10

<210> SEQ ID NO 58
<211> LENGTH: 10
<212> TYPE: DNA
<213> ORGANISM: ARTIFICIAL
<220> FEATURE:
<223> OTHER INFORMATION: template 21
```

```
<400> SEQUENCE: 58
ggaguugaag                                                              10

<210> SEQ ID NO 59
<211> LENGTH: 10
<212> TYPE: DNA
<213> ORGANISM: ARTIFICIAL
<220> FEATURE:
<223> OTHER INFORMATION: template T1

<400> SEQUENCE: 59
ggagaaccuu                                                              10

<210> SEQ ID NO 60
<211> LENGTH: 10
<212> TYPE: DNA
<213> ORGANISM: ARTIFICIAL
<220> FEATURE:
<223> OTHER INFORMATION: template T22

<400> SEQUENCE: 60
gcagaaccuu                                                              10

<210> SEQ ID NO 61
<211> LENGTH: 10
<212> TYPE: DNA
<213> ORGANISM: ARTIFICIAL
<220> FEATURE:
<223> OTHER INFORMATION: template T23

<400> SEQUENCE: 61
caggaaccuu                                                              10

<210> SEQ ID NO 62
<211> LENGTH: 10
<212> TYPE: DNA
<213> ORGANISM: ARTIFICIAL
<220> FEATURE:
<223> OTHER INFORMATION: template T24

<400> SEQUENCE: 62
ggagaaccuu                                                              10

<210> SEQ ID NO 63
<211> LENGTH: 10
<212> TYPE: DNA
<213> ORGANISM: ARTIFICIAL
<220> FEATURE:
<223> OTHER INFORMATION: template T25

<400> SEQUENCE: 63
ggggaaccuu                                                              10

<210> SEQ ID NO 64
<211> LENGTH: 10
<212> TYPE: DNA
<213> ORGANISM: ARTIFICIAL
<220> FEATURE:
<223> OTHER INFORMATION: template T26

<400> SEQUENCE: 64
gcagaaccuu                                                              10

<210> SEQ ID NO 65
<211> LENGTH: 10
```

```
<212> TYPE: DNA
<213> ORGANISM: ARTIFICIAL
<220> FEATURE:
<223> OTHER INFORMATION: template T27

<400> SEQUENCE: 65
caggaaccuu                                                          10

<210> SEQ ID NO 66
<211> LENGTH: 10
<212> TYPE: DNA
<213> ORGANISM: ARTIFICIAL
<220> FEATURE:
<223> OTHER INFORMATION: template T28

<400> SEQUENCE: 66
ggagaagaag                                                          10

<210> SEQ ID NO 67
<211> LENGTH: 10
<212> TYPE: DNA
<213> ORGANISM: ARTIFICIAL
<220> FEATURE:
<223> OTHER INFORMATION: template T30

<400> SEQUENCE: 67
gggucuagag                                                          10

<210> SEQ ID NO 68
<211> LENGTH: 10
<212> TYPE: DNA
<213> ORGANISM: ARTIFICIAL
<220> FEATURE:
<223> OTHER INFORMATION: template T31

<400> SEQUENCE: 68
gcagaagaag                                                          10

<210> SEQ ID NO 69
<211> LENGTH: 12
<212> TYPE: DNA
<213> ORGANISM: ARTIFICIAL
<220> FEATURE:
<223> OTHER INFORMATION: template T17

<400> SEQUENCE: 69
ggagaagaau uu                                                       12

<210> SEQ ID NO 70
<211> LENGTH: 12
<212> TYPE: DNA
<213> ORGANISM: ARTIFICIAL
<220> FEATURE:
<223> OTHER INFORMATION: template T18

<400> SEQUENCE: 70
ggagaagaac cc                                                       12

<210> SEQ ID NO 71
<211> LENGTH: 12
<212> TYPE: DNA
<213> ORGANISM: ARTIFICIAL
<220> FEATURE:
<223> OTHER INFORMATION: template T28 T4

<400> SEQUENCE: 71
```

```
<210> SEQ ID NO 72
<211> LENGTH: 12
<212> TYPE: DNA
<213> ORGANISM: ARTIFICIAL
<220> FEATURE:
<223> OTHER INFORMATION: template T4

<400> SEQUENCE: 72
ggagaagaag aa                                                            12

<210> SEQ ID NO 73
<211> LENGTH: 18
<212> TYPE: DNA
<213> ORGANISM: ARTIFICIAL
<220> FEATURE:
<223> OTHER INFORMATION: Syn5 promoter

<400> SEQUENCE: 73
ccattgggca cccgtaag                                                      18

<210> SEQ ID NO 74
<211> LENGTH: 18
<212> TYPE: DNA
<213> ORGANISM: ARTIFICIAL
<220> FEATURE:
<223> OTHER INFORMATION: Syn 5 modified promoter

<400> SEQUENCE: 74
cctcttggta cgcgcaag                                                      18

<210> SEQ ID NO 75
<211> LENGTH: 46
<212> TYPE: PRT
<213> ORGANISM: ARTIFICIAL
<220> FEATURE:
<223> OTHER INFORMATION: T7 RNAP

<400> SEQUENCE: 75

Glu Ile Ser Glu Lys Val Lys Leu Gly Thr Lys Ala Leu Ala Gly Gln
1               5                   10                  15

Trp Leu Ala Tyr Gly Val Thr Arg Ser Val Thr Lys Arg Ser Val Met
            20                  25                  30

Thr Leu Ala Tyr Gly Ser Lys Glu Phe Gly Phe Arg Gln Gln
        35                  40                  45

<210> SEQ ID NO 76
<211> LENGTH: 31
<212> TYPE: PRT
<213> ORGANISM: ARTIFICIAL
<220> FEATURE:
<223> OTHER INFORMATION: Syn5 RNAP

<400> SEQUENCE: 76

Glu Trp Ile Thr Arg Lys Val Thr Lys Arg Pro Val Met Cys Thr Pro
1               5                   10                  15

Tyr Gly Val Thr Met Ser Ser Ala Arg Gly Tyr Ile Arg Asp Gln
            20                  25                  30
```